US009993656B2

(12) United States Patent
Fried et al.

(10) Patent No.: US 9,993,656 B2
(45) Date of Patent: Jun. 12, 2018

(54) MAGNETIC NEURAL STIMULATOR AND METHOD OF ACTIVATION OF NEURAL TISSUE WITH SAME

(71) Applicants: Shelley Fried, Boston, MA (US); Seungwoo Lee, Boston, MA (US)

(72) Inventors: Shelley Fried, Boston, MA (US); Seungwoo Lee, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 242 days.

(21) Appl. No.: 14/895,757

(22) PCT Filed: Jun. 3, 2014

(86) PCT No.: PCT/US2014/040622

§ 371 (c)(1),
(2) Date: Dec. 3, 2015

(87) PCT Pub. No.: WO2014/197435

PCT Pub. Date: Dec. 11, 2014

(65) Prior Publication Data

US 2016/0129276 A1 May 12, 2016

Related U.S. Application Data

(60) Provisional application No. 61/830,379, filed on Jun. 3, 2013, provisional application No. 61/837,923, filed on Jun. 21, 2013.

(51) Int. Cl.
*A61N 2/00* (2006.01)
*A61N 2/02* (2006.01)
(Continued)

(52) U.S. Cl.
CPC .............. *A61N 2/006* (2013.01); *A61N 2/02* (2013.01); *A61N 1/0534* (2013.01);
(Continued)

(58) Field of Classification Search
CPC ................................................ A61N 2/00–2/12
See application file for complete search history.

(56) References Cited

U.S. PATENT DOCUMENTS 5,183,056 A 2/1993 Dalen et al.
5,338,286 A 8/1994 Abbott et al.
(Continued)

OTHER PUBLICATIONS

Abdeen, et al., Modeling of Magnetic Field Stimulation of Bent Neurons, IEEE Transactions on Biomedical Engineering, 1994, 41(11):1092-1095.

(Continued)

*Primary Examiner* — Thaddeus Cox
(74) *Attorney, Agent, or Firm* — Yakov Sidorin; Quarles & Brady LLP

(57) ABSTRACT

An electromagnetic neural stimulation device includes a biocompatible shaft and one or more microcoil systems inside the shaft. A microcoil system includes a microcoil (driven externally) that is complemented with a metallic element juxtaposed against the microcoil as a shield to non-uniformly affect spatial distribution of the strength of the magnetic field generated by the microcoil. The microcoil system is oriented at a position inside the shaft that is predetermined to place the microcoil system in the vicinity of target neurons once the shaft is inserted into the biological tissue. The angular orientation of the microcoil system is optionally varied to selectively stimulate different regions of the neural network.

12 Claims, 19 Drawing Sheets

(51) Int. Cl.
*A61N 1/378* (2006.01)
*A61N 1/05* (2006.01)
*A61N 1/36* (2006.01)

(52) U.S. Cl.
CPC ........ *A61N 1/0543* (2013.01); *A61N 1/36067* (2013.01); *A61N 1/3787* (2013.01)

(56) References Cited

U.S. PATENT DOCUMENTS

| | | | |
|---|---|---|---|
| 2009/0157147 A1 | 6/2009 | Cauller et al. |
| 2009/0254146 A1 | 10/2009 | Bonmassar et al. |
| 2011/0130615 A1 | 6/2011 | Mishelevich |
| 2012/0185020 A1 | 7/2012 | Simon et al. |

OTHER PUBLICATIONS

Amassian, et al., A Comparison of Corticospinal Activation by Magnetic Coil and Electrical Stimulation of Monkey Motor Cortex, Electroencephalogr. Clin. Neurophysiol., 1990, 77(5):390-401 [Abstract Only].

Amassian, et al., Focal Stimulation of Human Cerebral Cortex with the Magnetic Coil: A Comparison with Electrical Stimulation, Electroencephalogr. Clin. Neurophysiol., 1989, 74(6):401-416 [Abstract Only].

Basham, et al., Circuit and Coil Design for In Vitro Magnetic Neural Stimulation Systems, IEEE Transactions on Biomedical Circuits and Systems, 2009, 3(5): 321-331.

Bonmassar, et al., Microscopic Magnetic Stimulation of Neural Tissue, Nature Communications, 2012, 3: 921 (10 pages).

Chen, et al., Using Increased Structural Detail of the Cortex to Improve the Accuracy of Modeling the Effects of Transcranial Magnetic Stimulation on Neocortical Activation, IEEE Transactions on Biomedical Engineering, 2010, 57 (5):1216-1226 [Abstract Only].

Field Management Services, Shielding AC Magnetic Fields, http://www.fms-corp.com/mitigation_shielding.php4, date unknown, 1 page.

Gomez, et al., A Simulation of Focal Brain Stimulation Using Metamaterial Lenses, 2010, IEEE Antennas and Propagation Society International Symposium, pp. 1-4 [Abstract Only].

K&J Magnetics, Inc., What Does a Magnetic Field Look Like?, http://www.kjmagnetics.com/magneticfield.asp, date unknown, 4 pages.

Lee, et al., Activation of Retinal Ganglion Cells by Microcoil-Induced Magnetic Stimulation, Presentation Abstract, 2012, Investigative Ophthalmology & Visual Science, 53(14):5530.

Pu, et al., Simulation of Induced Electric Field Distribution Based on Five-Sphere Model Used in rTMS, J. Xray Sci. Technol., 2010, 18(1):57-67 [Abstract Only].

Tischler, et al., Mini-Coil for Magnetic Stimulation in the Behaving Primate, Journal of Neuroscience Methods, 2011, 194:242-251.

Tsuyama, et al., The Numeric Calculation of Eddy Current Distributions in Transcranial Magnetic Stimulation, Conf. Proc. IEEE Eng. Med. Biol. Soc., 2008, 2008:4286-4289 [Abstract Only].

Ueno, et al., Biomagnetic Measurements and Stimulation for Imaging and Estimation of the Functional Organization of the Human Brain, IEEE Transactions on Magnetics, 1993, 29(6):3309-3314 [Abstract Only].

Wu, et al., Inductive Generation of Arbitrary Waveforms for Electrical Stimulation Using Implantable Microcoils, Journal of Micromechanics and Microengineering, 2004, 14:1012-1021.

International Search Report and Written Opinion dated Oct. 16, 2014 for International Application No. PCT/US2014/040622.

MAGNETIC NEURAL STIMULATOR AND METHOD OF ACTIVATION OF NEURAL TISSUE WITH SAME

CROSS-REFERENCE TO RELATED APPLICATIONS

This patent application represents the national stage entry of PCT International Application No. PCT/US2014/040622 filed on Jun. 3, 2014 and claims priority from and benefit of the U.S. Provisional Patent Applications Nos. 61/830,379 filed on Jun. 3, 2013 and titled "Microscopic Magnetic Stimulation of Neural Tissue"; and 61/837,923 filed on Jun. 21, 2013 and titled "Magnetic Stimulation of Neurons" Disclosure of each of the above-identified provisional applications is incorporated by reference herein in its entirety.

STATEMENT REGARDING FEDERALLY SPONSORED RESEARCH

This invention was made with Government support under grant numbers RX000350 and EY019967, awarded by the National Institutes of Health. The Government has certain rights in the invention.

TECHNICAL FIELD

The present invention relates to stimulation of neurons and, in particular, to a system and method for stimulation of brain neurons and retinal neurons with magnetic field.

BACKGROUND

The most common treatment of Parkinson's Disease (PD) or other movement related disorders, who are not responsive to pharmacological intervention, is to stimulate the brain with small electrodes implanted into a region of the brain called the basal ganglia. The nuclei of the basal ganglia are found relatively deep within the brain. Accordingly, the treatment is often referred to as deep brain stimulation or DBS. It is now well established that high-frequency stimulation (~150 Hz) from DBS electrodes provides relief to patients with movement disorders and estimates indicate that about 100,000 patients already received these implants. Based on the success in the treatment of PD, the DBS technique is now under evaluation for a wide range of new treatment modalities.

Despite its success, DBS is not without side effects. For example, implanted electrodes limit the applicability of magnetic resonance imaging (MRI) to examination of a patient with implanted electrodes. (In particular, heating, induced by MRI-generated radio-frequency waves that interact with the conductive leads, generates induced currents that result in the loss of energy in the form of heat.)

Another important side effect results when stimulation from a DBS electrode causes inadvertent activation of those neurons that are not involved in coordination of movement. This occurs primarily through activation of passing axons—the thin, fibrous projections of nerve cells that establish communication among neurons. Axons from several different regions of the brain pass adjacently to the basal ganglia and are highly sensitive to the stimulus waveforms used in DBS. For example, activation of axons associated with facial nerves are thought to underlie the facial twitches observed in PD patients that have DBS implants.

Magnetic stimulation of neurons is an attractive alternative to conventional electric stimulation. To implement the magnetic stimulation, the flow of electric current through a coil is used to induce a magnetic field according to Faraday's Law. This magnetic field, in turn, induces an electric field that can activate neurons. One of the attractive elements of magnetic stimulation is that the magnetic field passes readily through non-ferrous materials including skin and bone. As such, the magnetic field is less affected by the inflammatory reactions that tend to occur around implanted stimulating devices. In addition, because establishing the flow of current through a coil requires a complete, closed electrical circuit, an implanted coil is much safer than a conventional DBS electrode for use in MRI systems as no current leakage occurs to the ambient (surrounding) medium. Unfortunately, until now the focus of research activities into magnetic stimulation was on large coils (several inches in diameter) that can only be used externally. Recently, Tischler et al. ("Mini-coil for magnetic stimulation in the behaving primate", *J. Neurosci. Methods, v.* 194, pp. 242-251, 2011) showed that coil diameters as small as 25 mm should activate neurons; although considerably smaller, such coils are still too large for implantation. More recently, a study by Bonmassar et al. (Microscopic Magnetic Stimulation of Neural Tissue, *Nat. Commun.*, Jun. 26 2012; 3:921 doi: 10.1038/ncomms1914) showed that coils diameters as small as 0.5 mm could activate neurons. Flow of current levels in excess of 1 A through such coils was estimated to generate field strengths of about 10 V/m, comparable to the known thresholds of neuronal activation.

Bonmassar et al. disclosed a micro-magnetic stimulator (U.S. 2009/0254146) that included a magnetic coil small enough to be implanted in the brain tissue. Specifically, the coil of Bonmassar is comparable in size to a DBS electrode and capable of modulating neural activity. Such coils (and the associated system) represent a potentially attractive alternative to conventional DBS electrodes because they are MRI compatible. As further demonstrated in the abovementioned "Microscopic magnetic stimulation of neural tissue" study, coils small enough to be implanted can in fact activate retinal neurons in vitro.

However, the problem of undesired activation, with such microcoils, of passing axons (causing unwanted physical reactions in the patients carrying implants) is not solved. Accordingly, there remains an unfulfilled need in a microsystem enabling magnetic stimulation of neural tissue in the brain that does not affect passing axons. In addition, the abovementioned system utilizes pulsatile stimulation that requires excessively high levels of current to elicit such activity.

SUMMARY

Embodiments of the invention provide a device for stimulating biological tissue such as, for example, brain tissue or retinal neuronal tissue. The device includes a biocompatible unit including a fluid-impenetrable shaft that extends along a longitudinal axis from a proximal end to a distal end. The shaft defines a hollow inside the shaft, which hollow is electrically-isolated from an ambient medium surrounding the shaft. The device may additionally include a plurality of electrical conductors extending along the longitudinal axis of the implant and at least one microcoil system having a microcoil. The microcoil is characterized by a microcoil axis, a longitudinal extent along the microcoil axis, and a diameter. The microcoil system(s) are being housed in the hollow of the shaft at corresponding pre-determined distance (s) from the distal end and oriented such as to define corresponding angle(s) between the microcoil axis (or axes)

and the longitudinal axis. The device may additionally include a coupling configured to electrically connect the microcoil system(s) through at least one electrical conductor to a power source to define an electrically-closed circuit enabled to drive the microcoil(s) to produce magnetic fields suitable for performing stimulation of chosen neuronal tissue. In a specific embodiment, at least one microcoil system of the device additionally includes at least one metallic element that is positioned adjacently to and extending along at least a portion of a perimeter of a loop of the corresponding microcoil and that enables a reduction of a strength of the magnetic fields (generated by the power source driven microcoil) in a direction transverse to said metallic element. Such metallic element may include a metallic sheet having a surface that is tangentially parallel to an outer surface of the microcoil. In addition or alternatively, such metallic element may include a metallic sheet having a surface that is substantially parallel to a surface defined by a loop of the corresponding microcoil. In a specific embodiment, the device is structured as a retinal and/or brain prosthetic device.

Embodiments of the invention also provide a device that includes a power source enabled to produce electric stimulus characterized by various waveforms (such as sinusoidal, sawtooth-like, ramps, square waveforms, pulses, for example) and a biocompatible unit defining a shaft with a hollow therein. The shaft has a longitudinal axis, and the shaft's hollow is electrically and fluidly insulated from an ambient medium surrounding the implant. In the follow at least one microcoil system embedded and operably connected to the power source to receive the electric stimulus to generate a magnetic field such as to induce a corresponding electrical field outside of the shaft that is suitable to perform stimulation of target neural tissue. At least one microcoil system includes a microcoil defined by at least one microcoil loop and a corresponding microcoil axis disposed at an angle with respect to the longitudinal axis. The angle characterizing the orientation of the microcoil in the hollow is determined at least in part based on directionality of target axons and/or based on at least one stereotactic mark associated with the target tissue (in a specific example, axons/dendrites of the brain tissue or bipolar cells of retinal tissue). At least one microcoil system of the device further contains at least one metallic element adjacent to and extending along at least a portion of a perimeter of a loop of the microcoil such as to enable a reduction of a strength of the magnetic fields (generated by the power source driven microcoil) in a direction transverse to said metallic element. In a specific case, the device is a retinal and/or brain prosthetic device.

Embodiments of the invention further provide a method for stimulation of target neural tissue with a system including a biocompatible shaft that has a distal end and a proximal end and a hollow therein. The method includes defining an electrical terminal at at least one microcoil system to receive electrical stimulus from a power source (wherein the at least one microcoil system includes a corresponding microcoil characterized by a microcoil axis); and disposing the at least one microcoil system within the hollow (which hollow is electrically and fluidly insulated from an ambient medium surrounding the shaft) such as to orient the microcoil axis at a first angle with respect to the longitudinal axis. The method additionally includes a step of formation the at least one microcoil system by juxtaposing a metallic shield element substantially tangentially parallel to a surface defined by the microcoil.

BRIEF DESCRIPTION OF THE DRAWINGS

The invention will be more fully understood by referring to the following Detailed Description of Specific Embodiments in conjunction with the generally not-to-scale Drawings, of which.

Unless identified otherwise, the same labels and numerals in the Drawings refer to the same elements of the Drawings.

DETAILED DESCRIPTION

The shortcomings of related systems for neural stimulations are overcome by providing a brain-tissue implant system that includes a non-ferrous tubular shaft made from a biocompatible material (such as polytetrafluoroethylene (PTFE; Teflon), polyurethane, polyimide, parylene, and liquid crystal polymers (LCPs) for example) that hosts in the hollow thereof a set of microcoils. A set generally includes one or more microcoils, an orientation of each of which is generally variable with respect to, for example, an axis of the shaft, and predetermined depending on a target positioning of such microcoil with respect to a region of brain tissue targeted for stimulation with the use of such microcoil (i.e., a position of a given microcoils along the shaft and the depth of implantation of the shaft in the brains tissue). A microcoil from the set may be complemented with a metallic micro-shield juxtaposed against a portion of the microcoil such as to alter the distribution of magnetic field produced by such microcoil in relation of spatial orientation of the target tissue around the implanted shaft.

Conventionally, the functional electrical stimulation has been carried out using commercially available electrode arrays. The electrodes depolarize neurons and activate the underlying area. The electrodes by their fundamental nature tend to preferentially stimulate substantially all neurons and fibers within a small volumetric region around each given electrode, without any well-defined preference. In contradistinction, the use of a set of magnetic coils (the orientation of each of which can be varied) by itself facilitates preferential activation over a certain direction, with the current having a mirror-image shape of the current in the coil. Neurons can be activated or not depending on the direction of the magnetic field, and the spatial distribution of the magnetic field around a coil to which it pertains. Further, even better defined selectivity of activation can be achieved by varying a position and/or orientation of the ferrous shield accompanying the coil, thereby enabling a modality for preferentially spatially-defined targeting and more selective stimulation of neurons.

Micromagnetic stimulation system and method structured according to embodiments of the invention has several advantages over conventional electric stimulation. Not only such set of microcoils is MRI-compatible (when turned off) as microcoils are electrically isolated from near-by biological tissue by the walls of the non-ferrous shaft, thereby limiting the amount of heat induction: the brain tissue, being exposed only to the biocompatible material of the shaft, does not experience unnecessary inflammation.

Figure 1A:
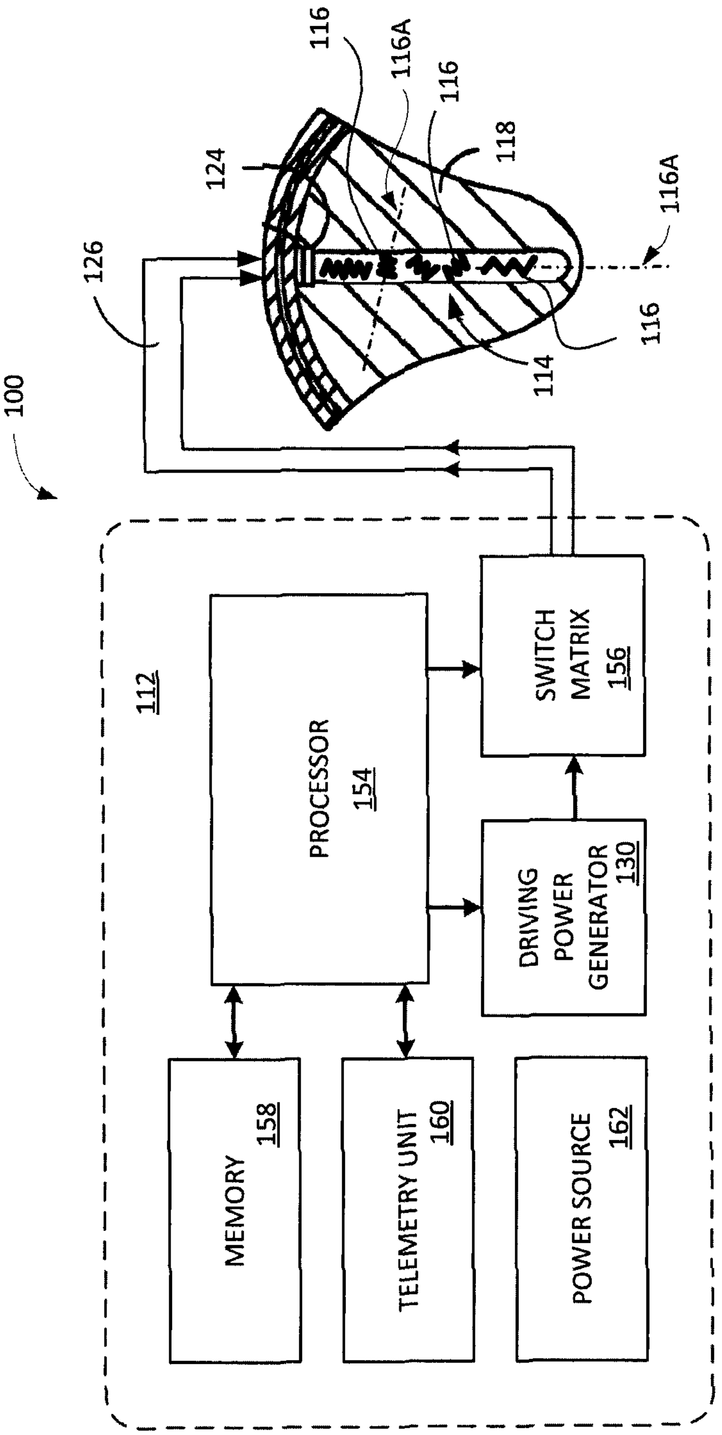
FIG. 1A is a diagram schematically presenting a neural stimulation system containing an array of microcoil systems.
Figure 1B:
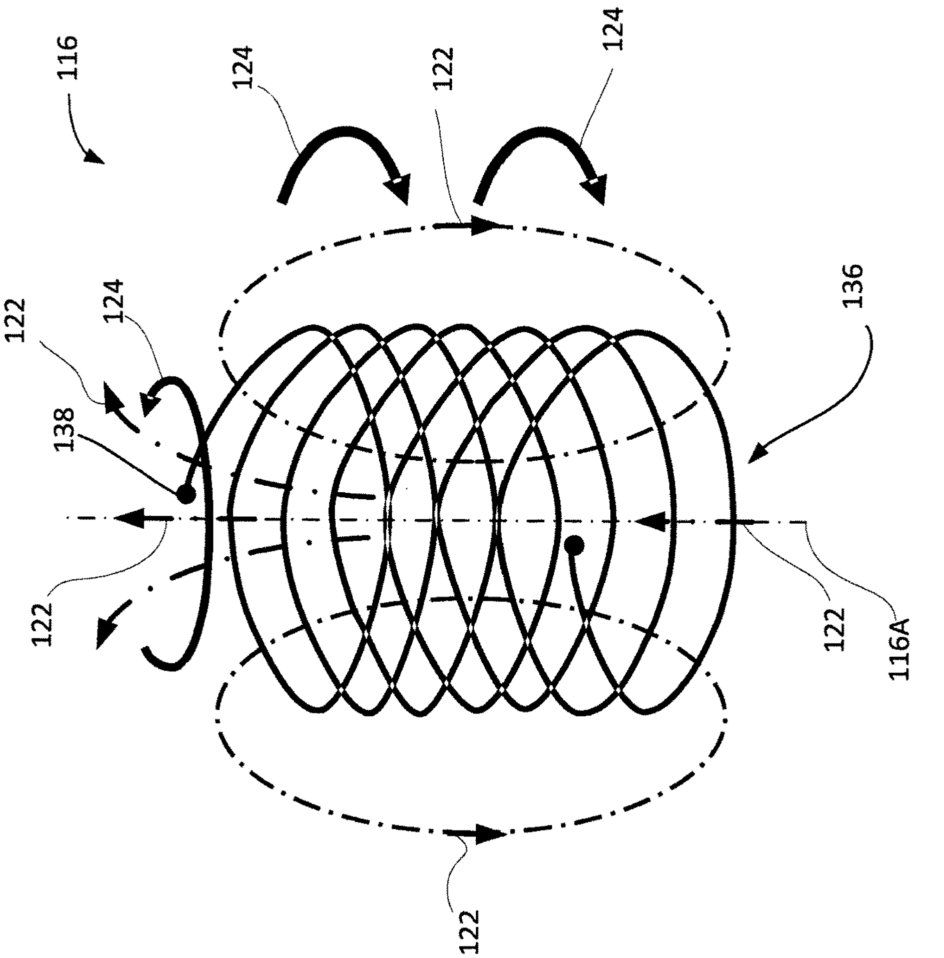
FIG. 1B is a diagram of an embodiment of a microcoil with indicators of generated fields.

Referring initially to FIGS. 1A and 1B, a tissue stimulation system 100 includes a stimulator 112 coupled to a device 114 (which may be structured as an implantable device, without reference to any particular structure) that contains a set of electromagnetic microcoils 116 (each having a respectively corresponding axis 116A) that are disposed inside the device 114. The stimulator 112 includes a drive power generator 130 that generates electrical stimuli (such as, for example, a sinusoidal or rectangular wave of a given duration, or pulses) for delivery to a targeted stimulation site in the brain tissue 118 via the device 114 as a result of installation of the implant 114 into the tissue. The stimulator 112 includes a drive power generator 130 that is enabled to generate electrical current (for example, in the form of pulses) for activation of at least one of the microcoils 116 when the device has been delivered to a targeted stimulation site in the brain tissue 118. The electrical pulses cause a given microcoil 116 to produce magnetic field with a characteristic spatial distribution indicated, with traces 122, in FIG. 1B. For example, a magnetic field vector in the middle of the coil is directed substantially co-linearly to the microcoil axis. The magnetic field, in turn, induces electrical currents (indicated with traces 124).

In the simplest implementation, as in further reference to FIGS. 1A and 1B, a microcoil 116 may be shaped as three-dimensional spiral 136 including loops of a metallic wire and having electrical terminals 138. The space between at least some of the individual loops may be optionally and at least partially filled with a dielectric material (not shown). Alternatively or in addition, a microcoil 116 may be overcoated with a dielectric material such as, for example polytetrafluoroethylene (PTFE; Teflon), polyurethane, polyimide, parelyne or liquid crystal polymers (LCPs). These biocompatible materials can be used for coating of microcoils 116 as well as to construct the body of the biocompatible shaft of the device 114. In the embodiment in which a given microcoil is electrically connected to the stimulator 112 with via an electrical lead 126, the implant 114 also includes such' electrical conducting lead(s) or member(s) that are connected to the terminals 138 (not shown in FIG. 1B).

Figure 2:
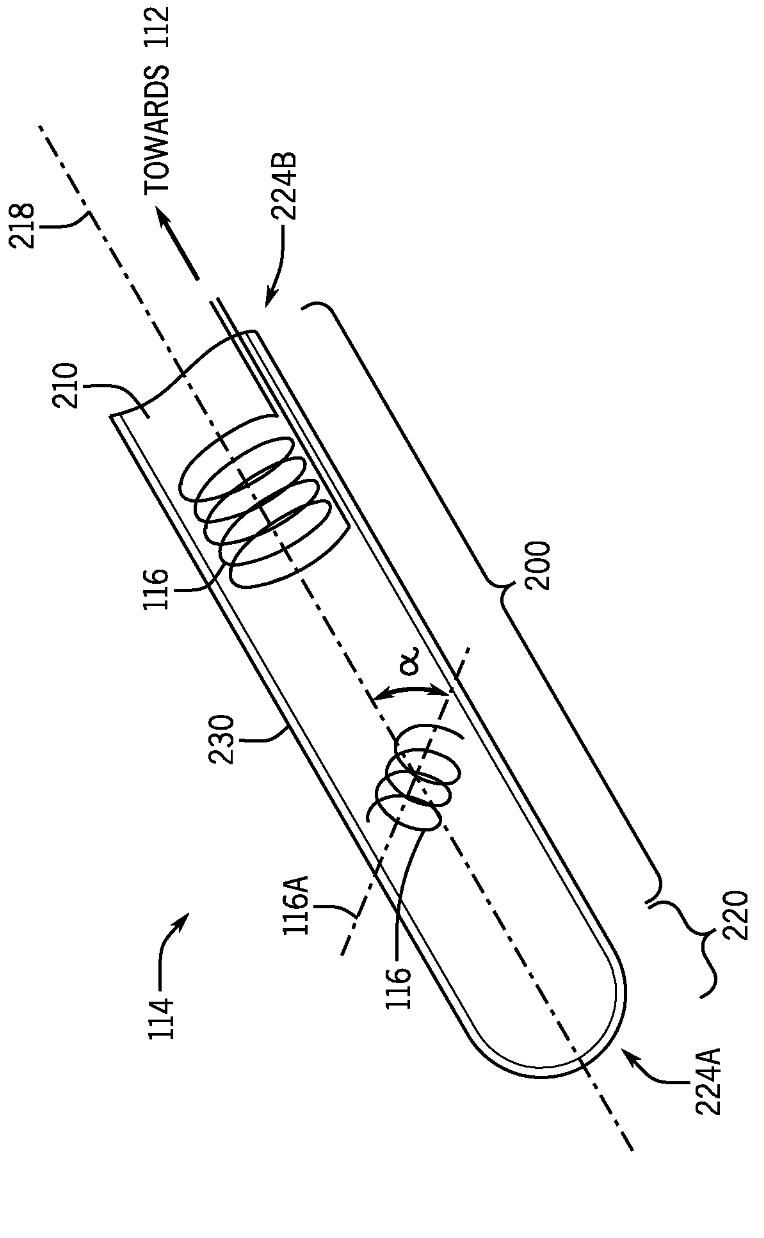
FIG. 2 is a diagram depicting schematically a shaft of an embodiment of the invention with a plurality of microcoil systems disposed in the hollow of the shaft.

In reference to FIG. 2 and in further reference to FIG. 1A, the device 114 is structured to define, when installed and/or assembled, an elongated hollow (tubular) portion 200 having an internal volume 210 bound by the wall and extended along the axis 218. In a specific case, the tubular body 200 may be substantially cylindrical, for example about 1.2 mm (or less) in outer diameter with an internal diameter of less than, for example, 1 mm. The device 114 also includes a cap portion 220 terminating and integrated with the tubular body portion 200 at a distal end 224A such as to physically separate the internal volume 210 from an ambient medium surrounding the device 114. The volume 210 inside the device 114 hosts a set of microcoils 116 (which includes at least one microcoil) that are disposed therein in similar or different orientations with respect to the axis 218 (as indicated schematically with angle ⍰).

In one embodiment, both the tubular portion 200 and the cap portion 220 are separately fabricated from a biocompatible and non-degradable material such as PTFE, polyurethane, polyimide, parylene, and LCPs. After the microcoils 116 have been positioned inside and along the length of the tubular portion 200, the tubular and cap portions are integrated (for example, sealed or molded) with one another to form a fluid-impenetrable shaft 230 that separates the ambient medium from the volume 210. In another embodiment, the shaft 230 is molded as a unitary element and then complemented with the set of microcoils 116 by disposing the microcoils inside the shaft through the proximal end 224B. The proximal end 224B of the shaft 230 of the device 114 may include a connector 124 structured to facilitate the electrical communication of the microcoils 116 with the stimulator 112.

Multiple spaced-apart microcoils 116 may be oriented differently from one another and form a set of microcoils queued along the axis 218 inside the shaft 230 with or without a direct contact with the internal surface of the shaft 230. Each of the microcoils is electrically coupled to the stimulator 112 via a corresponding coupling 126 (that may include at least one electrical lead or, alternatively, a wireless coupling). In another implementation, at least one microcoil 116 is disposed substantially coaxially with the axis 218 to produce a magnetic field penetrating into the target brain tissue 118 with neurons.

Figure 3A:
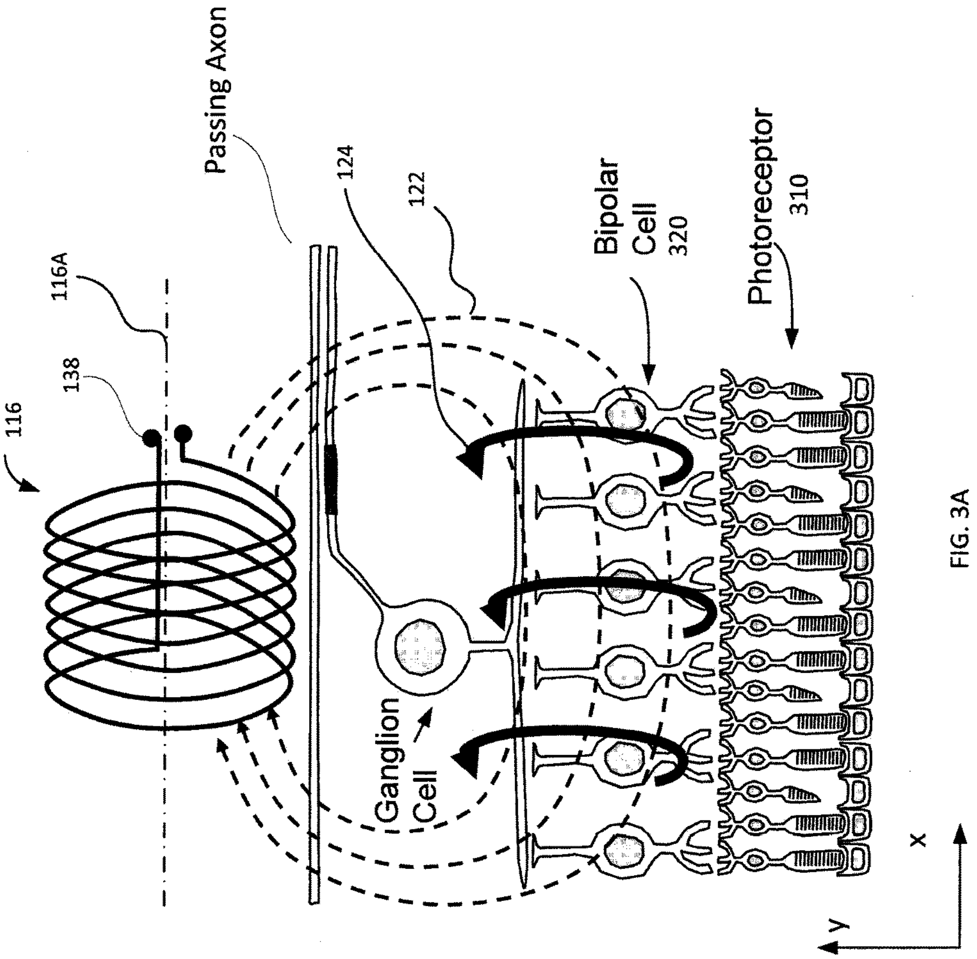
FIG. 3A is a diagram illustrating the interaction between a sheet of neurons and the fields generated by a microcoil that is oriented in parallel to the sheet of neurons.

It was unexpectedly empirically found that the orientation of a given coil 116 strongly influences which ones of local neurons and passing axons (of the brain tissue surrounding the portion of the device 114 with the coil 116) become activated. In reference to FIG. 3A, for example, it was discovered that the microcoil 116 that is positioned with its main axis 116A substantially parallel to a sheet of neurons (which sheet extends, as shown, along the xz-plane, in reference to, for example, the retina as shown by the photoreceptor(s) 310) substantially does not affect or activate passing axons. Instead, the operation of such microcoil affects only the local neurons by activating them. It is contemplated that the mechanism underlying such selective effect stems from the orientation of the induced electric fields/currents 124, which is/are substantially perpendicular to the surface of the tissue and penetrates into the tissue. The operation of the so-oriented microcoil is not effective in activating of passing axons because the orientation of the passing axons is essentially parallel to the retinal surface, but, instead, the operation of the coil 16 of FIG. 3A activates those neurons the orientation of which is perpendicular to the retinal surface (such as, for example, bipolar cells 320 in the retina). The release of synaptic neurotransmitter from the activated bipolar cells modulates the activity of nearby neurons, especially ganglion cells, without simultaneously activating passing axons. As a result, the induced neural activity is kept substantially spatially restricted. In other words, when the induced electric field is substantially parallel to the retinal surface, the passing axons (which are also parallel to the retinal surface) are not activated and, therefore, the side effects that would otherwise arise from the activation of passing axons are not present or at least substantially reduced. (An example of a side effect is provided by unwanted activation of other retinal neurons positioned outside of target area, caused by retinal stimulation of passing axons, which unwanted activation reduces the quality of prosthetic vision.)

Figure 3B:
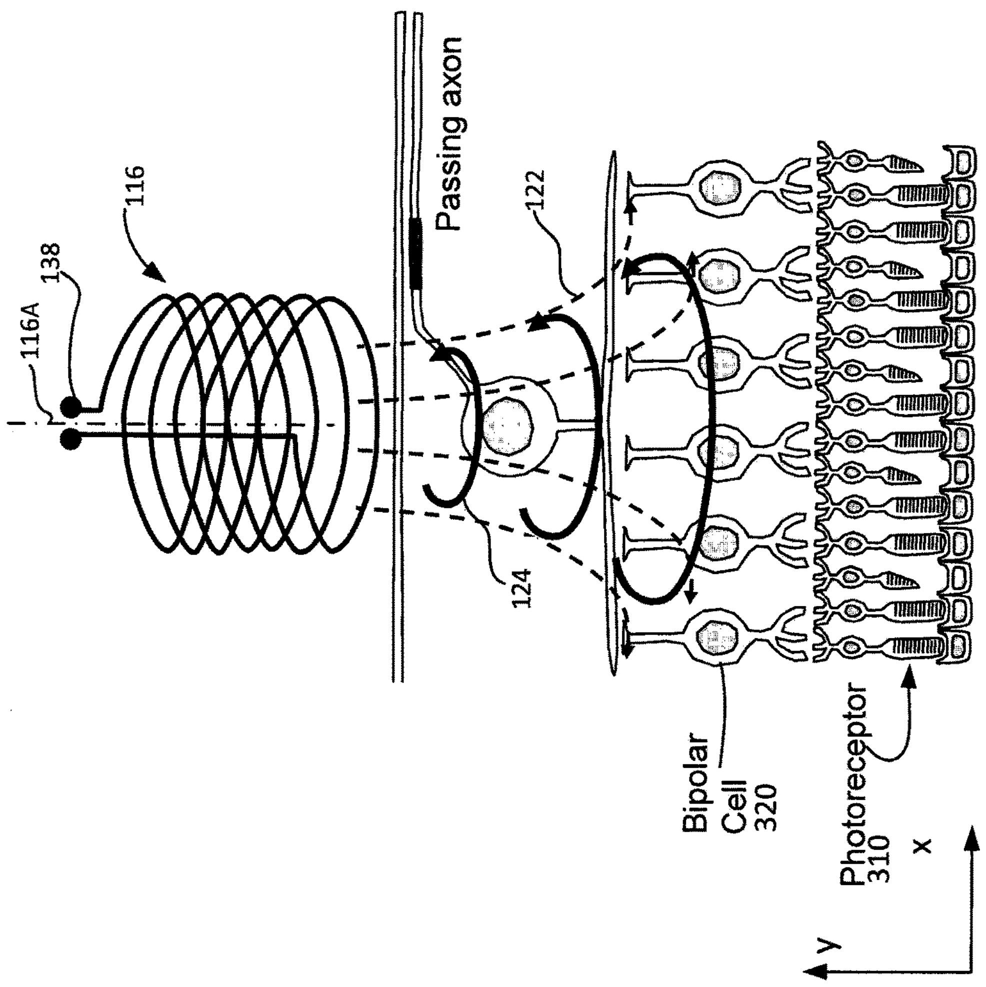
FIG. 3B is a diagram illustrating the interaction between a sheet of neurons and the fields generated by a microcoil that is oriented substantially transversely to the sheet of neurons.

The rotation of the coil 116 to a position in which its main axis 116A is substantially perpendicular to the sheet of neurons (as shown in FIG. 3B) results in an induced electric field 124 that is oriented substantially parallel to the retinal surface (xz-plane). Accordingly, in this configuration, the passing axons are activated without simultaneous activation of the bipolar cells. An intermediate orientation of the microcoil (defined by an angle between zero and 90 degrees formed by the microcoil axis 116A and the direction of the passing axon) produces an intermediate result.

Figure 4:
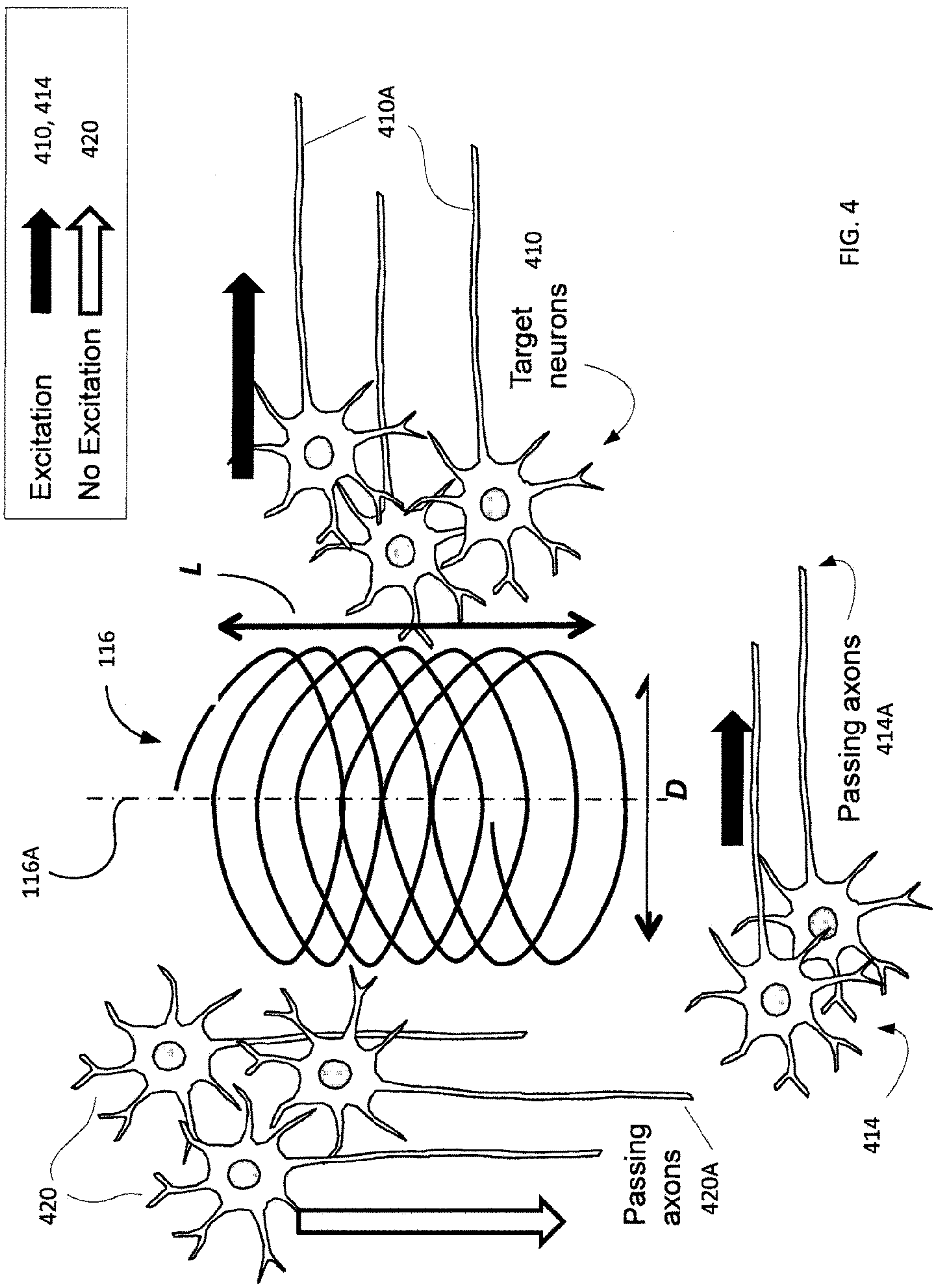
FIG. 4 is a diagram illustrating the dependence of neural excitation on mutual orientation between a microcoil system and the targeted neurons.

Embodiments of the invention make use of this unexpected discovery in that, according to an embodiment of the invention, a set of microcoils 116 of the device 114 (of FIG. 1A, 2) is generally assembled to include microcoils of different sizes and/or shapes and/or orientations that are judiciously chosen to target the activation of pre-determined group(s) of neurons. In reference to FIG. 4, for example, a coil 116 having a nominal diameter D and length L that is positioned (inside the device 114) in a proximity to a group of neurons with heterogeneous organization will effectively activate those neurons 410, 414 the axons 410A, 414A of which run substantially perpendicular to the main axis 116A of the coil (i.e., substantially along the direction of the electric field induced by the magnetic coil 116). However, the strength of the activating force for those neurons 414 directly below the coil can be minimized by adjusting the dimensions of the coil. For example, if the length of the coil is significantly greater than its diameter (for example, a coil with the length of 3 to 5 mm and the outer diameter of about 1 to 1.2 mm), the affected/activated neurons will be the neurons 410 located and/or distributed along the length L of the coil 116 but not necessarily the neurons 414, which are distributed substantially along a plane transverse to the axis 116A (along or near the area transverse to the axis 116A) and which have the diameter D). On the other hand, making the coil diameter significantly larger than its length (for example, the diameter of about 1 mm to 1.2 mm with the length of about 0.01 mm to 0.2 mm) would result in shifting the preponderance of activation more towards those cells and axons that are close, for example about 0.05 mm to about 0.2 mm, to the coil edges (i.e. 414), and not those axons along the length of the coil (410 and 420).

Figure 8A:
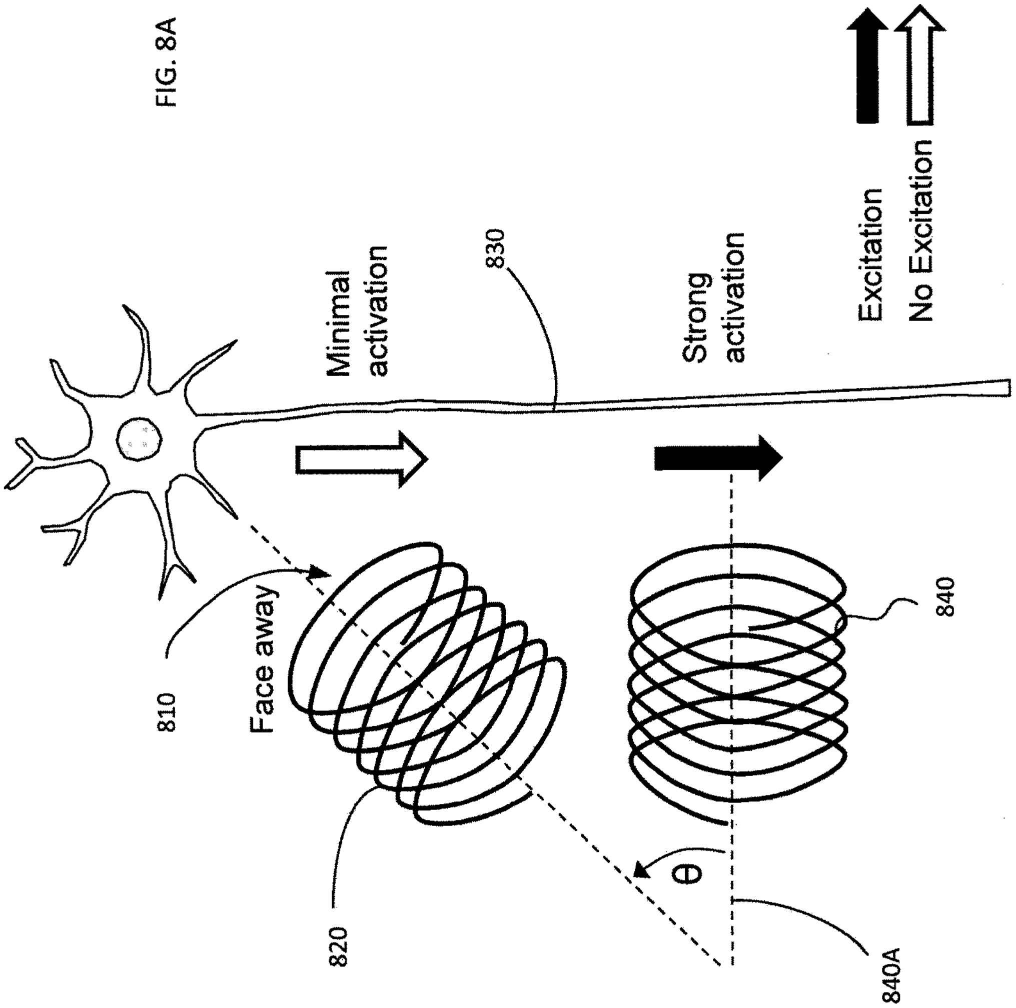
FIGS. 8A and 8B provide illustrations to activation of neural tissue with microcoils employing different design and/or different spatial orientation with respect to the neural tissue.
Figure 8B:
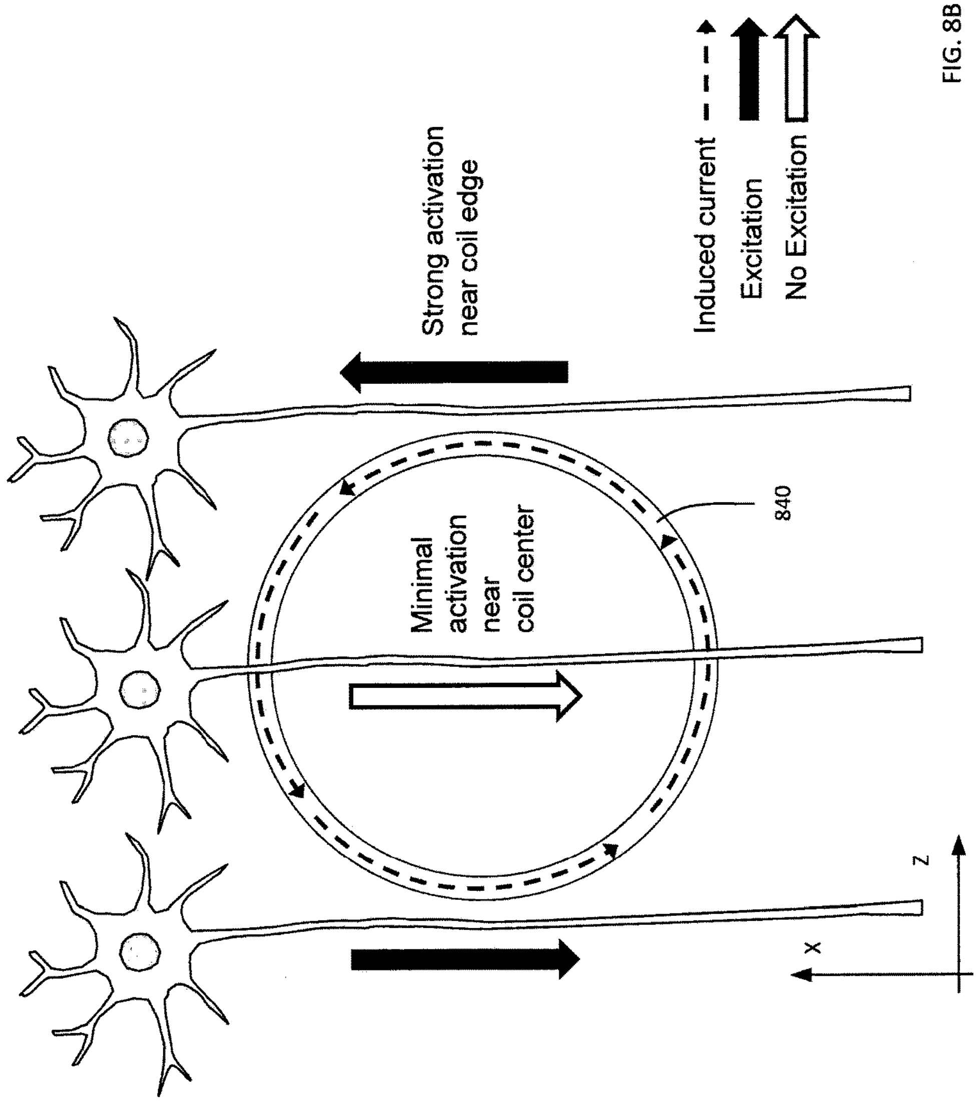
Figure 9:
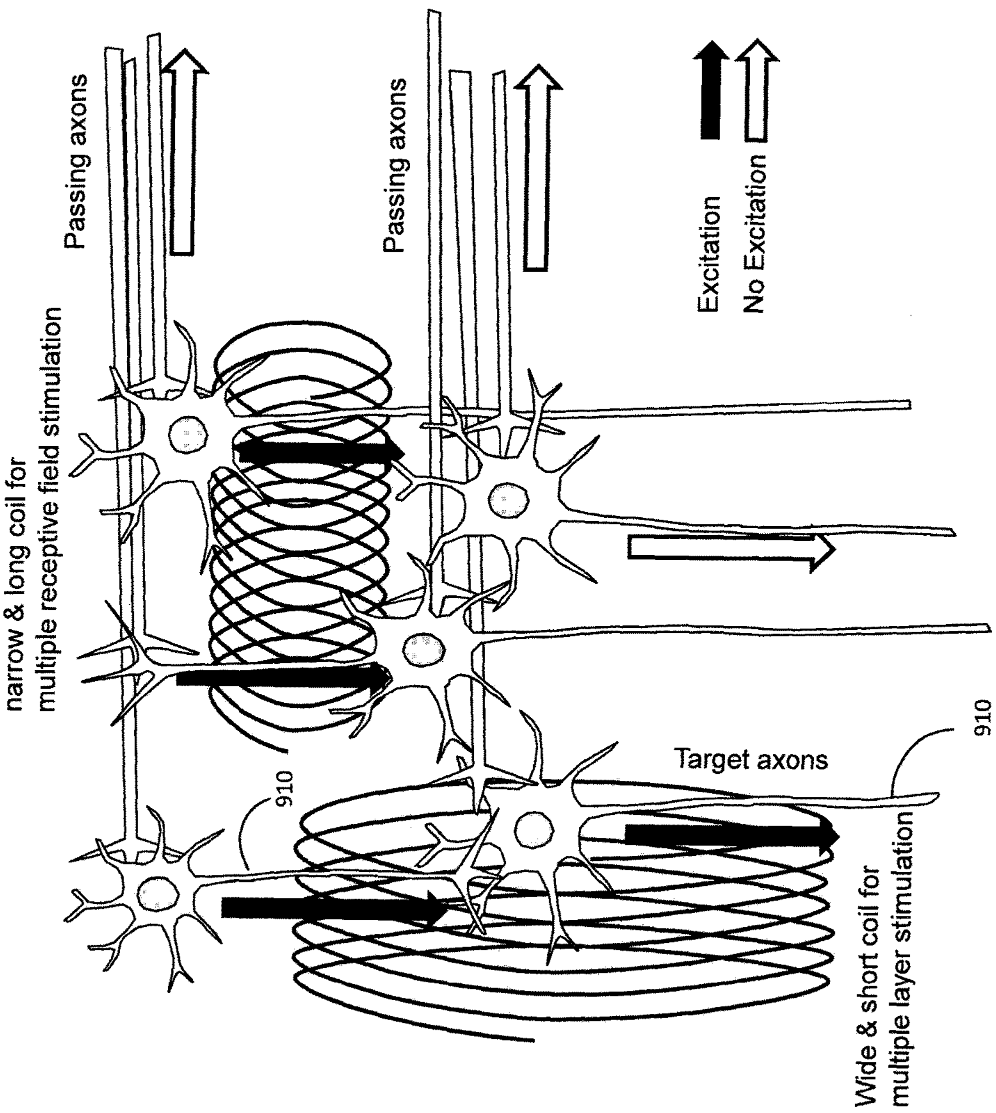
FIG. 9 is a diagram providing illustration to stimulation of sheets of neurons.

Further, according to an embodiment, the orientation of a particular coil inside the shaft 230 of the device 114 can be judiciously optimized so that the regions associated with coil edges (i.e., the regions more likely to activate passing axons) 'face away' from potential axon targets when the implant 114 has been inserted. This situation is schematically illustrated in FIGS. 8A, 8B where edge region 810 of the coil 820 is turned away (at an angle θ) with respect to the axon 830, causing the reduction (or even substantial lack) of the excitation of the axon 830 as a result of the operation of the coil 820. This situation is compared to the coil 840 oriented with its axis 840A substantially perpendicularly to the axon 830. The operation of so-oriented coil causes the strong activation of the axon 830. Analogously, other coil structures and positioning may be employed. For example, short coils with large diameters (such as those having a length-to-diameter ratio of about 0.1 or a few tenths, for example) can be employed in the shaft 230 for other applications in which the simultaneous activation of multiple layers (two or more layers) of neuronal circuits is desirable. This situation is illustrated in FIG. 9, where each of the neuron layers 910, 912 is about 1 mm high and about 300 to 500 microns wide.

In a related embodiment, a microcoil contains an auxiliary shielding component judiciously structured to restrict the spatial distribution of the electric filed produced by the microcoil such as to avoid the activation of targeted passing axons. Owing to the fact that a magnetic field passes readily through non-ferrous materials such as biological tissue but is blocked or shielded by metal, in the embodiment 500 of FIG. 5 the microcoil 116 can be optionally complemented by at least one metallic shielding component (referred to herein interchangeably as shield) such as, for example, (i) a longitudinal shield 510 disposed along the length and outside of the coil 116 and/or (ii) a transverse shield 520 disposed substantially transversely to the microcoil axis 116A such as to cap, crown, or end of the microcoil 116.

In one implementation, the longitudinal shield 510 is a metallic plate defining a surface that is substantially tangentially parallel to a surface defined by the loops of the coil 116 (in a simple case—a substantially cylindrical surface). Alternatively, the longitudinal shield 510 may be a metallic plate having a substantially flat surface. The shield 510 is dimensioned to cover a predetermined number of the loops of the coil 116 and is disposed adjacently to the coil 116. The thickness of the shield may range from about 0.0005 mm to about 0.05 mm. Width, length, and curvature of bend of a microcoil loops are generally adjusted to the dimension s of the microcoil. In one example, the shield has the thickness of about 0.001 mm, the width of about 0.5 mm, the length of about 1 mm, and the radius of curvature of about 0.25 mm.

Figure 5:
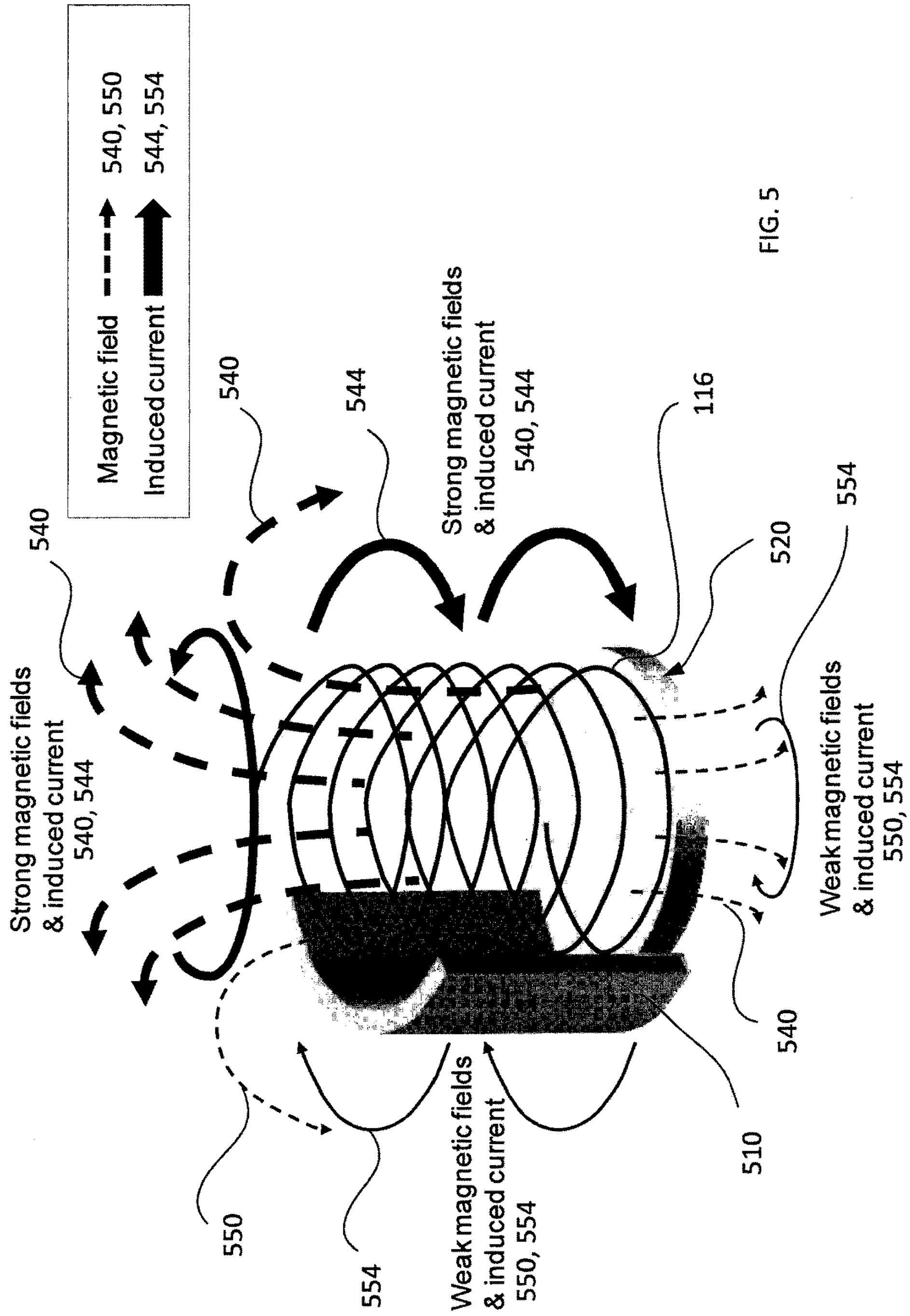
FIG. 5 is a diagram depicting an embodiment of a microcoil system of the invention including longitudinal and transverse magnetic shields.

Optionally, the surface of the shield 510 is separated from the coil 116 by a dielectric material (not shown). For example, the microcoil 116 and the longitudinal shield 510 (positioned with respect to the microcoil 116 at a predetermined location along the length of the microcoil) can be laminated to one another with a sheet of plastic material between them, thereby defining a fixed structure. Alternatively or in addition, the combination of the shield 510 and the microcoil 116 can be overcoated with a plastic material (not shown). In another example, the plastic sheet separating the longitudinal shield 510 from the microcoil 116 is structured to enable a mutual repositioning of the shield 510 and the coil 116 with respect to one another in azimuthal direction (about the axis 116A of the coil 116). For instance, the surface of the plastic sheet separator can include a relief structure guiding at least one loop of the coil 116. The transverse shield 520 is also a metallic plate (optionally separated from the loop by a dielectric material and/or overcoated with the dielectric material) disposed at a predetermined distance from the terminating loop of the coil to block at least a portion of the aperture of the coil 116 defined by a coil's loop. For example, the transverse shield 520 may be juxtaposed with the microcoil 116 as shown in FIG. 5 such as to cover essentially all of the area defined by the diameter of the microcoil or, alternatively, be disposed such as to leave a portion of this are uncovered (not shown). Overall, the components of the coil system 500 can be molded into, laminated, or encased in the housing dielectric material (not shown).

As indicated schematically in FIG. 5 with the use of numerals 540, 550, the use of at least one of the longitudinal and transverse shields 510, 520 in conjunction with the microcoil 116 spatially modulates the magnetic field produced by the microcoil 116. Accordingly, the use of t least one of such shields is envisioned to facilitate the activation of different sections of the neuron population with the implant 114 containing the shielded microcoil (for example, with respect to activation of neurons associated with the retina of the subject). Each of the shields 510, 520 alters the magnetic field 540, as well as the current 544 that would be produced by the microcoil in absence of the shield(s), and reduces its strength resulting in a weaker magnetic field 550 and the weaker induced current 554, thereby essentially reducing or even blocking the activation of those neurons/axons that are adjacent to and/or closest to the shield(s). Accordingly, positioning the transverse shield 520 across an end of the coil 116 could be used to eliminate or at least reduce the formation of the magnetic field extending from that end, thereby eliminating or at least reducing the possibility of neuronal activation. Similarly, covering a portion (for example, one-half) of the rounded portion of the coil 116 with the longitudinal shield 510 could be used to ensure that the neuronal stimulation is preferential. An example of the preferential neuronal stimulation is provided, for example, by directing/shaping the magnetic field to target the basal ganglia and not in the other direction (e.g. towards passing axons).

It is appreciated that a specific shape and/or specific dimensions of any of the longitudinal and transverse shields 510, 520 do not affect the principle of the invention and that different three-dimensional structures can be envisioned and tailored to ensure that activation is restricted to only desirable portions of the brain. For example, a 'cradle'-shaped shielding element could be used to block both ends of the coil as well as one-half of the length of the coil (i.e. the half facing away from a targeted neuronal structure). This would effectively block neuronal activation in all directions other than in the direction of the intended target.

The actual number and arrangement of the microcoils 116 inside the shaft 230 of the implant 114 may vary with specific design or application considerations and are considered to be within the scope of the present invention. Other design considerations, such as the geometry (e.g., size, shape, etc.) and placement of the microcoils 116, may be adjusted depending on the amount or location of neural stimulation for a particular treatment. The induced electric field is a sum of the electric fields induced by each microcoil, and therefore, by changing the driving currents of individual microcoils 116, the area of neural stimulation can be shaped and targeted.

Figure 7B:
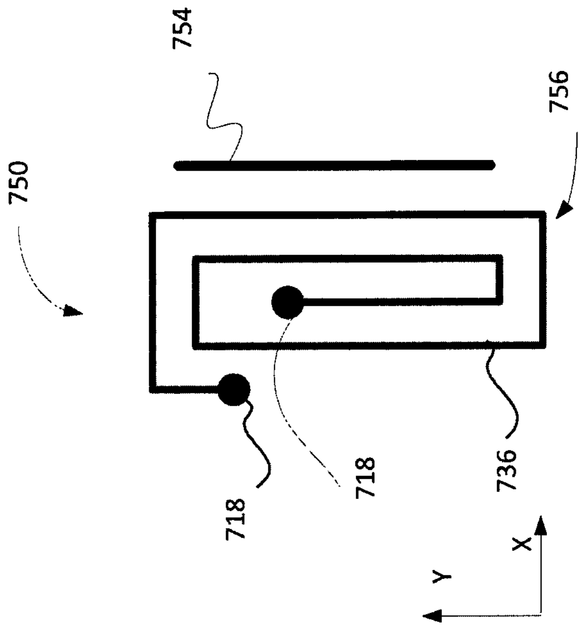
FIGS. 7A and B illustrate schematically alternative embodiments of a substantially two-dimensional microcoil and a substantially-two-dimensional microcoil system, respectively.
Figure 7A:
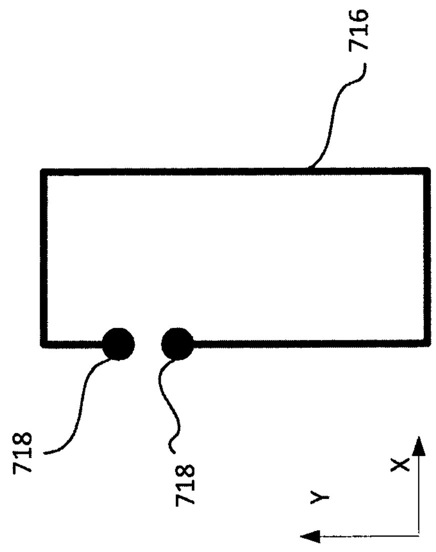

In one alternative embodiment, in reference to FIGS. 7A and 7B, a microcoil 700 may structured in a surface (for example, as shown, in xy-plane) and be shaped, in the simplest case, as a ring or loop 716 of a metallic trace on a flexible (for example, mylar) substrate having electrical terminals 718. Alternatively, FIG. 3B, the microcoil system 750 may be structured as a substantially two-dimensional (2D) spiral 736 including multiple loops of metallic traces 716, in which multiple loops of the microcoil are defined in the same plane. A shielding component of such flat or 2D microcoil system 750 is shown as another metallic element or trace 754 adjacent to and extending along at least a portion of a perimeter of a loop of the microcoil 756. While shown with a substantially rectangularly-shaped loops, neither the structural principle nor principle of operation of the microcoil system 750 depends on the shape and/or size of any of the loops of the corresponding microcoil. In practice, a multilevel microcoil system structures can be assemble by appending, stacking on top of one another, or otherwise spatially cooperating the microcoil systems such as the microcoil system 750. In practice, multiple layers in a multilevel microcoil system containing multiple 2D microcoils and/or multiple loops of a given 2D microcoil can be separated from one another by electrically insulating layers and each layer may contain differently structured shielding component(s) 754. In one example, a given 2D microcoil system can be structured as an integrated chip on a flexible substrate.

Referring again to FIG. 1A, the stimulation system 112 may further include a processor 154 to set the parameters of driving electrical signals (in a specific example of a sinusoidal driving signal—the amplitude, frequency, and duration of the sinusoid; in a specific example of electrical pulse(s)—amplitude, pulse width, and pulse rate parameters of stimulation pulses) applied to the implant 114. The processor 154 may be realized by one or more microprocessors, digital signal processors (DSPs), Application-Specific Integrated Circuits (ASIC), Field-Programmable Gate Arrays (FPGA), or other equivalent integrated or discrete logic circuitry. The stimulation system 100 may further include a switch matrix 156 to apply the stimulation pulses across selected microcoils 116 or microcoil systems 616 within a single portion of the implant 14 or within two or more implant portions. The stimulation pulses may be applied in a bipolar or multipolar arrangement, in which multiple microcoils 116 are selected for delivery of stimulation pulses, for example, across or among different microcoil pairs or groups. Alternatively, the stimulator 12 may include multiple pulse generators 130, each coupled to and controlling a given series of microcoils 116.

A tangible non-transitory computer-readable memory 158 may be provided to store instructions for execution by the processor 154 to control the pulse generator 133 and the switch matrix 156. For example, the memory 158 may be used to store programs defining different sets of stimulation parameters and microcoil combinations. Other information relating to operation of the stimulator 112 may also be stored. The memory 58 may include any form of computer-readable media such as random access memory (RAM), read only memory (ROM), electronically programmable memory (EPROM or EEPROM), flash memory, or any combination thereof.

A telemetry unit 160 supporting wireless communication between the stimulator 112 and an external programmer and/or display device (not shown) may be provided. The processor 154 controls the telemetry unit 160 to receive programming information and send operational information. Programming information may be received from an external clinician programmer or an external patient programmer. The wireless telemetry unit 160 may receive and send information via radio frequency (RF) communication. The display device may be configured to form a visually-perceivable representation of the results of interaction between the field(s) generated by the microcoil systems of the implant 114 and the target neural tissue.

A power source 162 delivers operating power to the components of the stimulator 112 including the microcoils 116. The power source 162 may include a rechargeable or non-rechargeable battery or a power generation circuit to produce the operating power. In some embodiments, battery recharging may be accomplished through proximal inductive interaction between an external charger and an inductive charging coil within the stimulator 112. In other embodiments, operating power may be derived by transcutaneous inductive power generation, e.g., without a battery.

Figure 6:
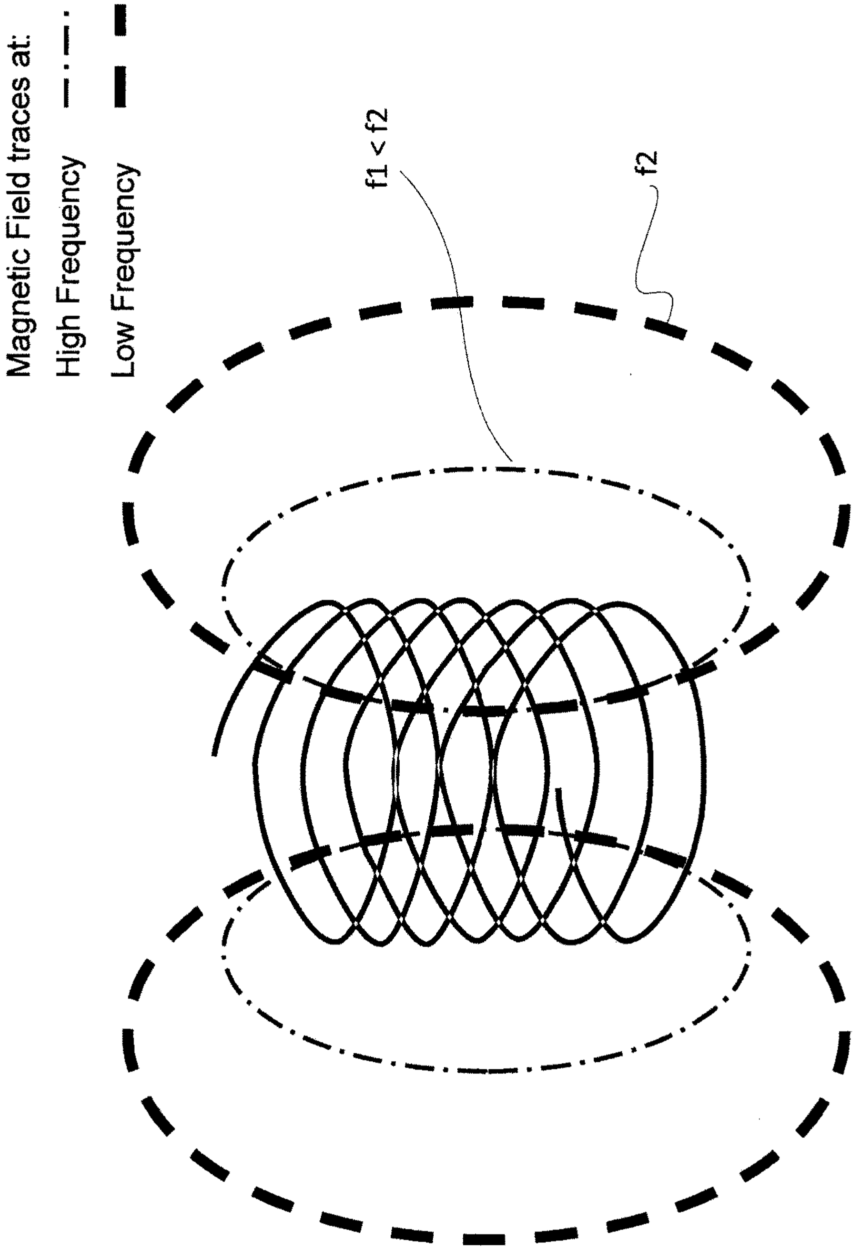
FIG. 6 is a diagram illustrating an embodiment of the invention directed to controlling a depth of penetration of the excitation field into the neural space.

In a related embodiment, the processor 154 is specifically programmed to govern the operation of the stimulator 112 to cause the amplitude and/or frequency modulation of the magnetic field(s) generated by at least one of the microcoils 116. In a specific case, for example, and in reference to the schematic of FIG. 6, the so-caused modulation of frequency of the magnetic field is defined to vary the standard depth ▯ of penetration of the magnetic field into the ambient medium according to $$D_P \sim \frac{1}{\sqrt{\pi f \mu \sigma}}$$

wherein represents the distance away from the coil at which the strength of induced currents is about 37% of the strength of the currents at the surface of the coil's end, f denotes the coil input pulse frequency, ▯ is the electrical conductivity of the ambient medium, and μ is the magnetic permeability of the ambient medium. Accordingly, the implementation of such embodiment of the device enables the variability of the volume of the neuron stimulation space associated with one or more portions of the implant 114 (where the microcoil at point is located) in a controllable fashion.

At least some elements of a device of the invention can be controlled, in operation with a processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the disclosed inventive concepts. For example, at least two individual 3D microcoil system similar to that discussed in reference to FIG. 5 can be pre-determinately and judiciously positioned inside the hollow of the shaft 230 of the implant 115 such as to ensure that their respectively corresponding axes 116A are substantially intersecting (or at least passing extremely close to one another) at a point P located at a given distance outside of the shaft. As the magnetic field produced by a given microcoil is the strongest along the axis of the coil, the electric fields (generated through the Faraday's law) from the two coils in the spatial region adjacent to and/or surrounding the point P will be reinforcing one another, thereby creating a region in which the neural stimulation can be carried out at very high levels of electrical fields and currents. For example, two microcoils of the two microcoil systems housed inside the hollow of the shaft of an embodiment of the implant may be pre-determinately oriented such that their individual axes either substantially cross one another or pass in the proximity of one another outside of the shaft; the intersection of the two axes defines a region that will be subjected to enhanced magnetic stimulation therefore, is a region of selective targeting. In one implementation, the individual axes of the coils pass each other while separated by a predetermined distance (for the purposes of a non-limiting example—a distance comparable with a diameter of an individual coil). In another embodiment, at least one of the microcoil systems of the embodiment of the invention can be driven by the drive power generator 130 generating a sinusoidal waveform. It is also appreciated that a particular size and/or shape of a given 3D microcoil such as the microcoil 116 of FIG. 6 does affect which types of neurons and/or their subcomponents. Some empirical evidence indicates that the use of a long and thin 3D microcoils system within the hollow of the shaft of the embodiment of the invention may facilitate avoiding of the activation of passing axons.

Figure 10:
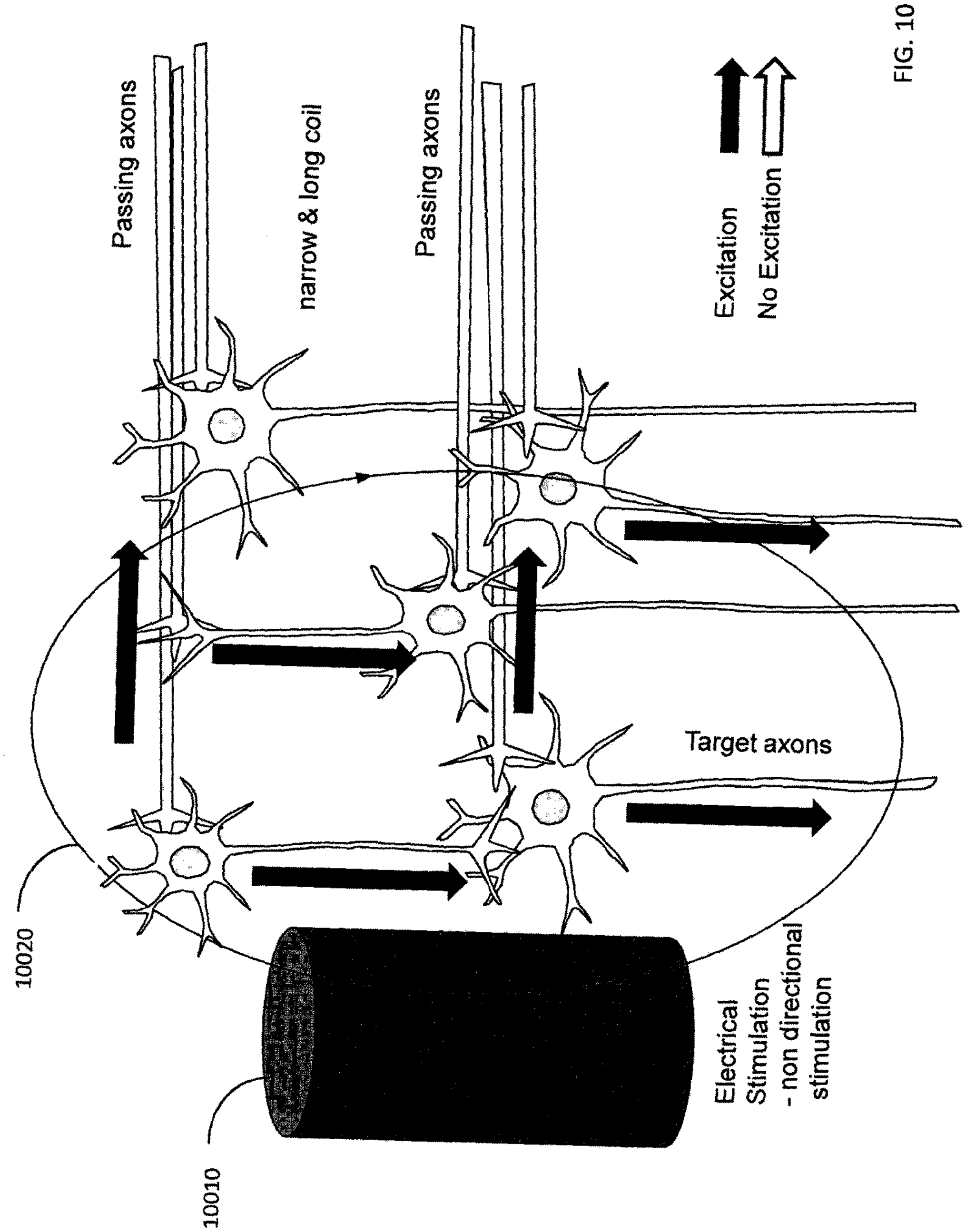
FIG. 10 is a diagram providing an illustration of spatially non-selective neural activation with a conventional electrode.

For the purpose of comparison with the proposed embodiments of the invention, FIG. 10 provides an illustration of stimulation of the neural tissue with an electric field formed by an implanted electrode 10010. The stark differences between the operation of such conventionally used stimulating element and that of the present invention is apparent: the stimulation with directly formed electrical field 10020 is not spatially selective and simply does not afford or provide for the stimulation of a pre-determined target neural tissue. Instead, no matter the mutual orientation between the axons and the electrode 10010, any axon (whether target or passing) located within the region penetrated by the electric field 10020 (with the strength above a certain threshold) will be stimulated.

The use of the term "substantially" as applied to a specified characteristic or quality descriptor means "mostly", "mainly", "largely but not necessarily wholly the same" such as to reasonably denote language of approximation and describe the specified characteristic or descriptor so that its scope would be understood by a person of ordinary skill in the art. The use of this term both in the present disclosure and the appended claims neither implies nor provides any basis for indefiniteness and for adding a numerical limitation to the specified characteristic or descriptor. For example, a reference to a vector or line being substantially parallel to a reference line or plane is to be construed as such vector or line extending along a direction that is the same as or very close to that of the reference line or plane (for example, with angular deviations from the reference direction that are considered to be practically typical in the art). As another example, the use of the term "substantially flat" in reference to the specified surface implies that such surface may possess a degree of non-flatness and/or roughness that is sized and expressed as commonly understood in the art in the specific situation at hand.

Figure 11:
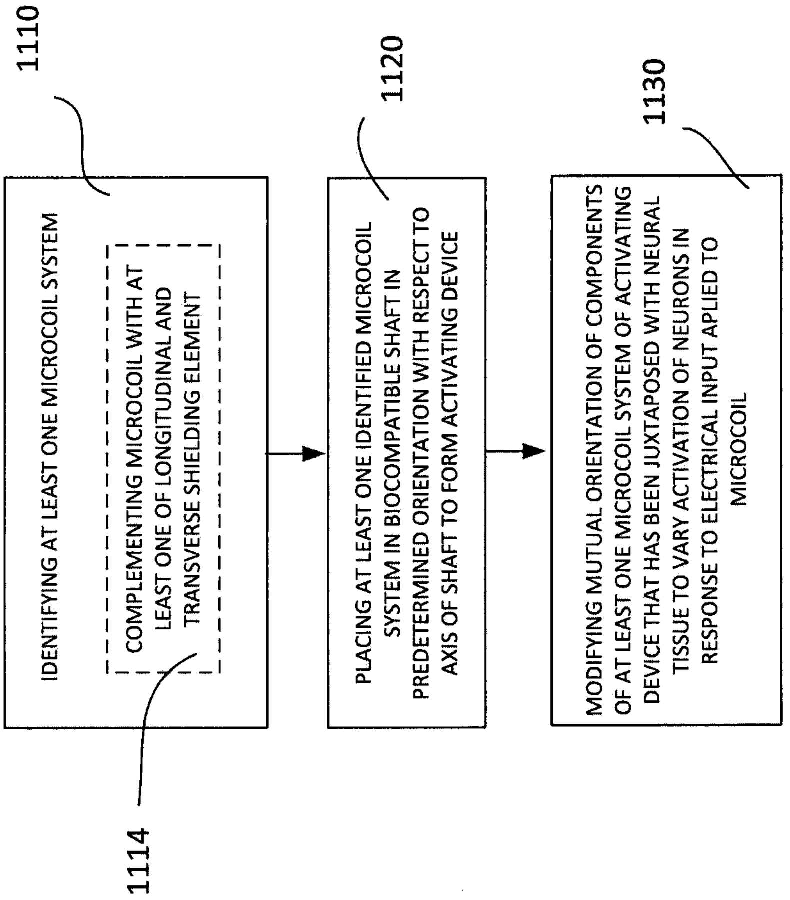
FIG. 11 is a flow chart representing steps of the method according to an implementation of the invention.

A flow-chart schematically illustrating a method according to one embodiment o the invention is shown in FIG. 11. Here, at step 1110, at least one microcoil system is chosen that includes a microcoil (characterized by length, diameter, number of loops and other typical microcoil characteristics) and an electrical terminal to which an electrical source is connected during the operation of the chosen microcoil system. The microcoil system may be optionally structured, at 1114, such that the microcoil is complemented with a metallic shield element juxtaposed against and substantially tangentially parallel to a surface defined by the microcoil. The metallic shield may be either longitudinal (structured and disposed similarly to the element 510 of FIG. 5) or transverse (structured and disposed similarly to the element 510 of FIG. 5) with respect to the axis of the microcoil in question, separated from the loops of the coil with dielectrically insulating material, and be fixed or movable with respect to the coil The neural tissue activating device containing such at least one chosen microcoil system is then assembled, as 1120, by disposing the chosen microcoil system(s) within the hollow of a biocompatible shaft structured such as provide both the electrical and fluid isolation of the contents of the shaft from the ambient medium surrounding the shaft. In so disposing the microcoil system(s), each of the corresponding microcoils is oriented at a corresponding pre-determined angle with respect to the longitudinal axis of the shaft. In a specific case, the orientation of a given microcoil can be determined with the use of a MRI scan and/or microelectrode recording(s) of the target tissue. Once the activating device has been placed in proximity of neural tissue and once a microcoil of at least on chosen microcoil system has been activated with external input to generate the corresponding electrical field, the mutual orientation of components of at least one chosen microcoil system (for example, the mutual orientation between the metallic shielding element and the microcoil and/or the orientation of the microcoil with respect to the axis of the shaft) can further be varied, 1130, to impart variable influence on identified portion of neural tissue.

Figure 12:
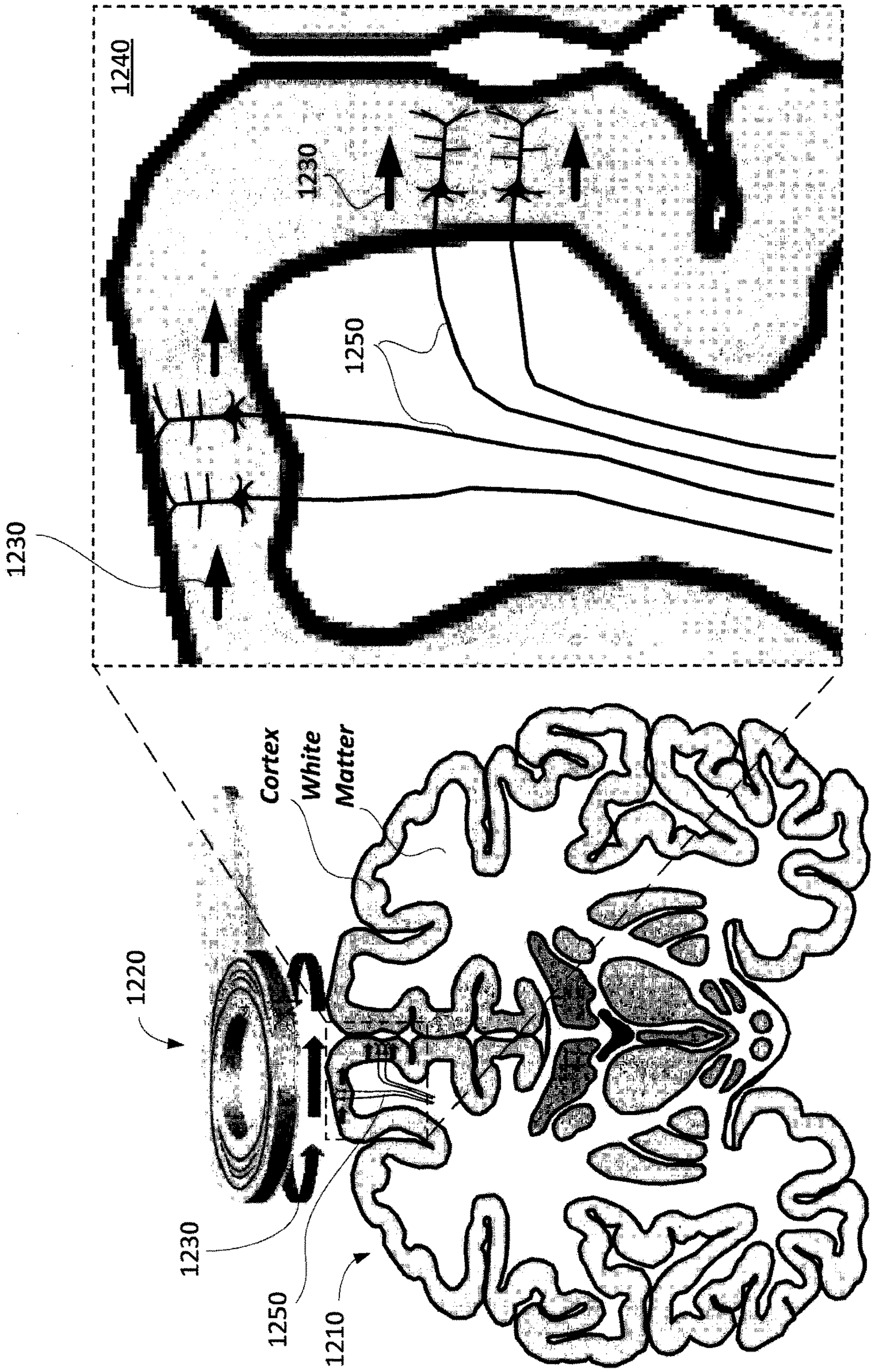
FIG. 12 is a diagram with a blown-up portion shown in inset, schematically illustrating conventional TMS and depicting how the transcranial magnetic stimulation works in brain stimulation, in the cross-sectional view of human brain structure (coronal section) and TMS coil positioned over the target area. Induced current is created inside the brain and oriented along the rim of TMS coil. Inside the target area (shown in inset) some cortical neurons (i.e. layer V pyramidal neurons) are aligned with the induced current, whereas other neurons are not.

FIG. 12 offers a schematic illustration of conventional application of the TMS in brain stimulation, in the cross-sectional view of a coronal section of brain structure 1210 and TMS coil 1220 positioned over the target area. Induced current (shown with arrows 1230) is created inside the brain and oriented along the rim of the TMS coil 1220. Inside the target area 1240 (shown in inset) some of the cortical neurons 1250 (i.e. layer V pyramidal neurons) are aligned with the induced current, whereas other neurons are not.

Figure 13:
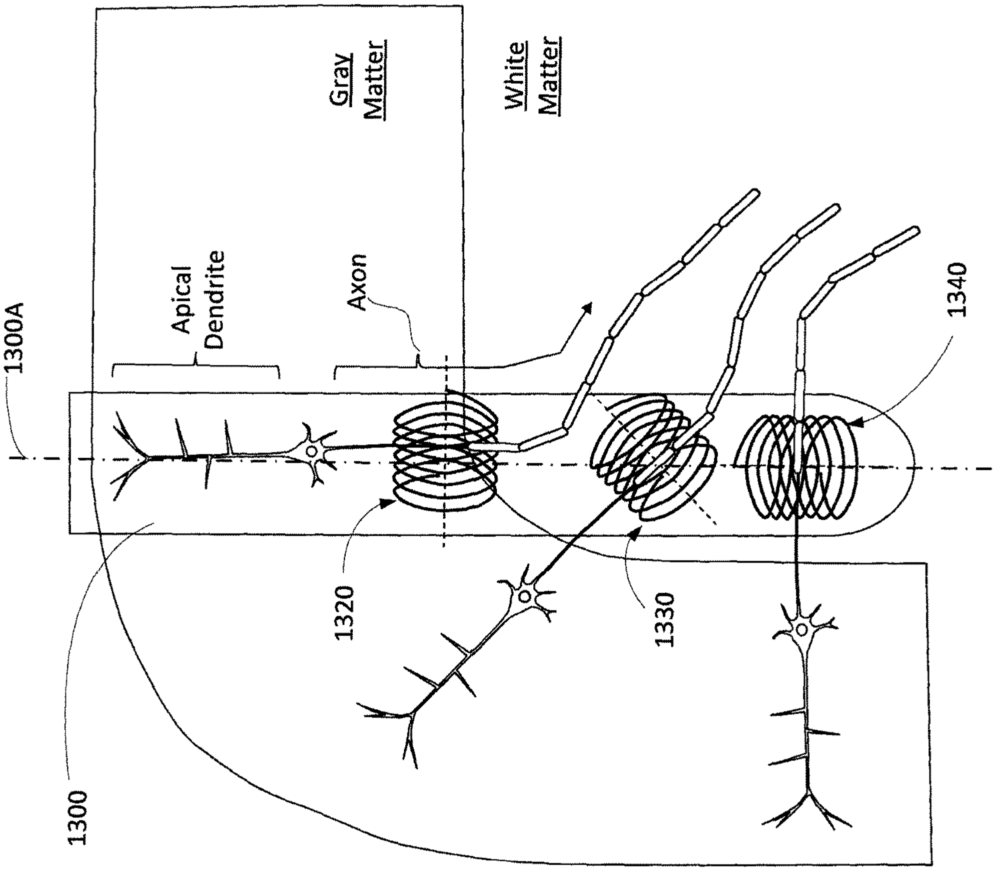
FIG. 13 provides an example of cortical neuron stimulation on axon fiber with implanted device structured according to an embodiment of the invention. The device has micro-coils that have pre-determined orientations so that the directions of induced current are parallel to the directions of targeted axon fibers of cortical neurons. AS a result. each cortical neuron is separately excited.

FIG. 13 provides an example of the use of an embodiment 1300 of the device of the invention (such as, for example, the embodiment 114 described in reference to FIGS. 1A, 1B, 2) for cortical neuron stimulation of axon fiber. Different microcoils 1320, 1330, 1340 (each having a corresponding pre-determined orientation with respect to the device axis 1300A and operable/activatable, with the stimulator unit 112 shown in FIG. 1A, simultaneously with or independently from the rest of the microcoils) cause corresponding induced currents judiciously directed in a pre-determined spatial orientation (for example, in parallel) with respect to the targeted axon fibers of cortical neurons. As a result, each cortical neuron may be separately targeted and excited.

Figure 14:
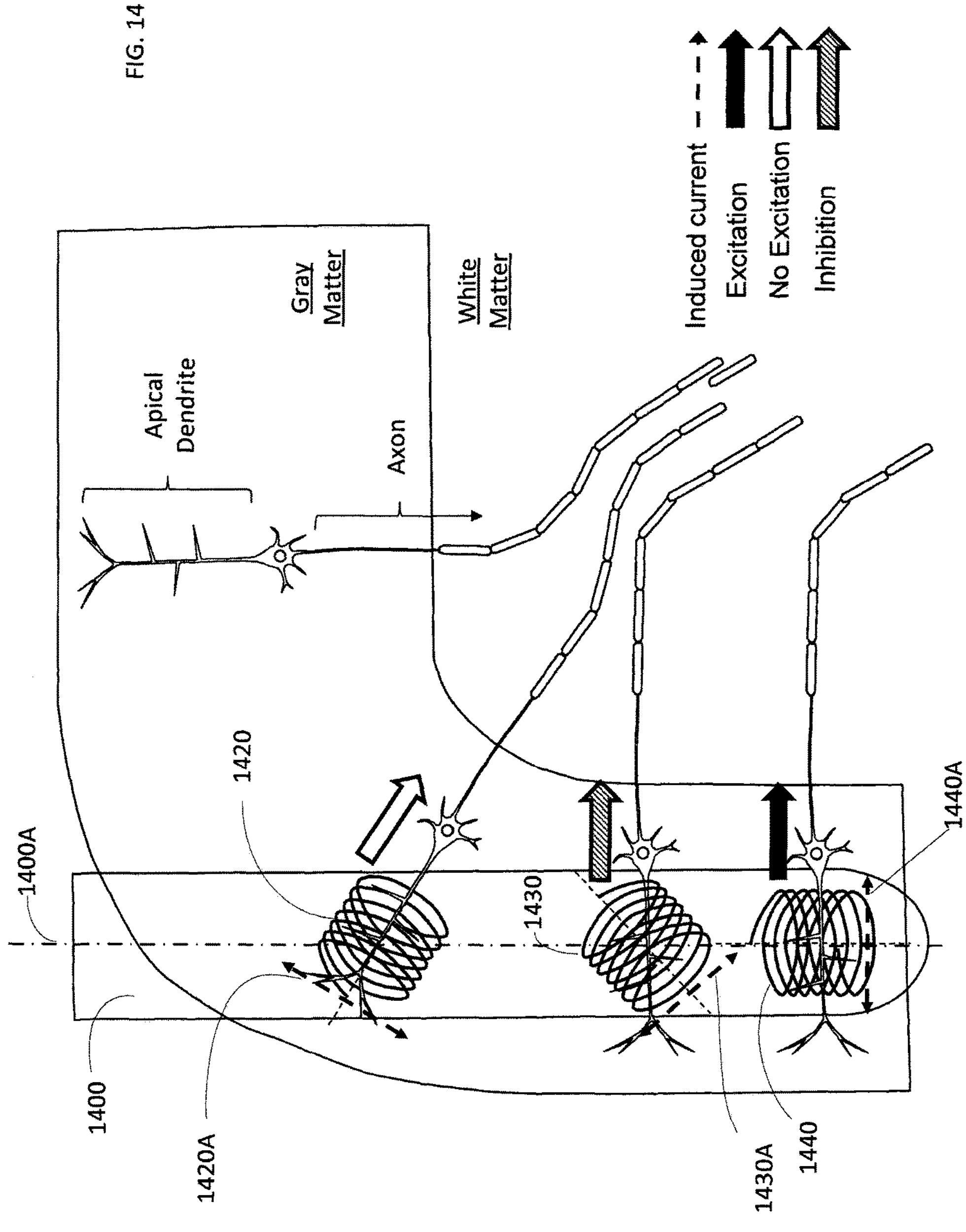
FIG. 14 provides a diagram illustrating an example of cortical neuron stimulation on apical dendrite with the implanted device structured according to an embodiment of the invention. The device has micro-coils that have pre-determined orientations so that the directions of induced currents are either parallel (A), oblique (B), and/or perpendicular to the directions of targeted apical dendrites of cortical neurons. With parallel orientation, the targeted cortical neuron is strongly excited. With oblique orientation, the targeted cortical neuron is strongly inhibited. With perpendicular orientation, the targeted cortical neuron is not excited.

FIG. 14 provides a diagram schematically illustrating an example of cortical neuron stimulation of apical dendrite with a device 1400 structured according to an embodiment of the invention. The device 1400 has micro-coils 1420, 1430, 1440 that have pre-determined spatial orientations so that the directions of respectively corresponding induced currents 1420A, 1430A, 1440A are, respectively, either perpendicular, oblique, or parallel to the directions defined by targeted apical dendrites of cortical neurons. In parallel orientation (1440A), the targeted cortical neuron is strongly excited. In oblique orientation (1430A), the targeted cortical neuron may be inhibited (the strength of inhibition depends on the angle between the vector of induced current and the direction of the targeted apical dendrite). In perpendicular orientation (1420A), the targeted cortical neuron is not excited.

Figure 15:
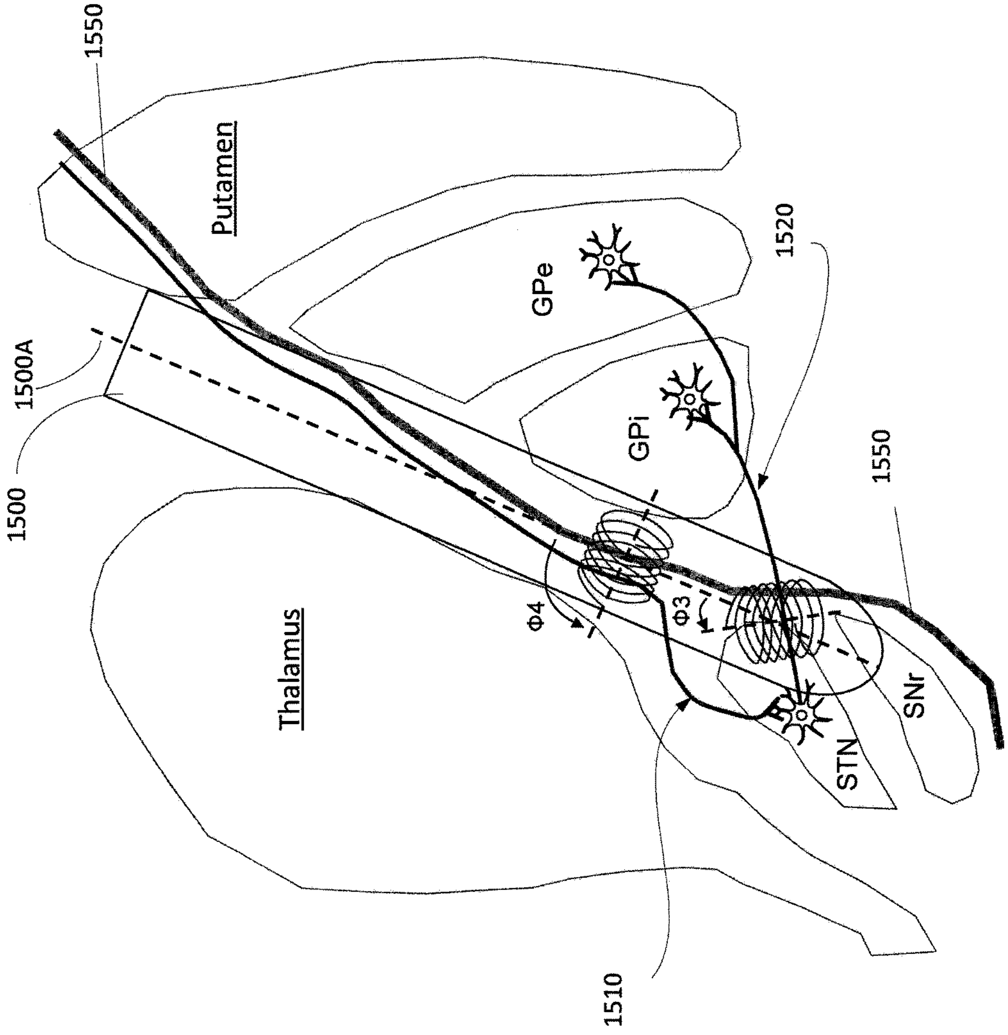
FIG. 15 is a schematic showing an example of subcortical neuron stimulation (Deep Brain Stimulation). The embodiment of the device has micro-coils with pre-determined orientations of corresponding axes, so that the directions of induced currents are parallel to the directions of targeted axon fibers. The axon fibers that connect STN with GPi/GPe are selectively excited by the micro-coil with the angle of $\phi_3$, whereas the passing axon bundles are avoided. (The passing axon bundles may be selectively excited by a micro-coil oriented at a different angle, instead.

FIG. 15 is a schematic showing an example of sub-cortical neuron stimulation (Deep Brain Stimulation). Again, individual microcoils of the device 1500 of the invention have various orientations with respect to the axis of 1500A of the device, so that the vectors of respectively corresponding induced currents are oriented such as to target pre-determined axon fibers (for example, an afferent axon 1510 to a STN neuron and/or an efferent axon 1520 from an STN neuron). As shown, the efferent axon fibers that connect STN with GPi/GPe are selectively excited by the micro-coil with the angle of $\phi_3$, the afferent axon fibers that connect STN with GPi/GPe are selectively exited by the microcoil oriented at $\phi_4$, whereas the excitation of the passing axon bundles 1550 of other brain circuits (e.g., internal capsule) is avoided.

Figure 16A:
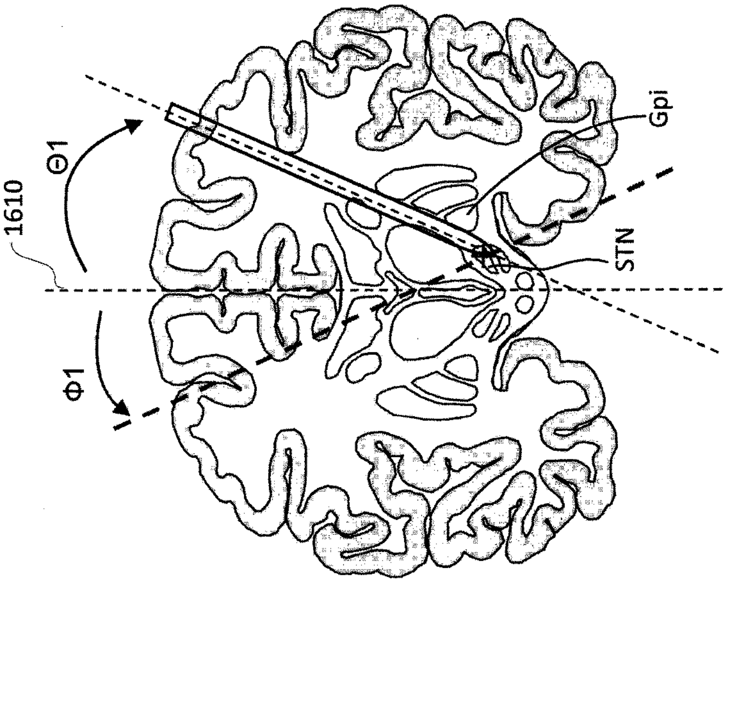
FIGS. 16A and 16B illustrate an example of orientation of a microcoil in a device of the invention with respect to defined stereotactic mark, in coronal plane view and mid-saggital plane view, respectively.
Figure 16B:
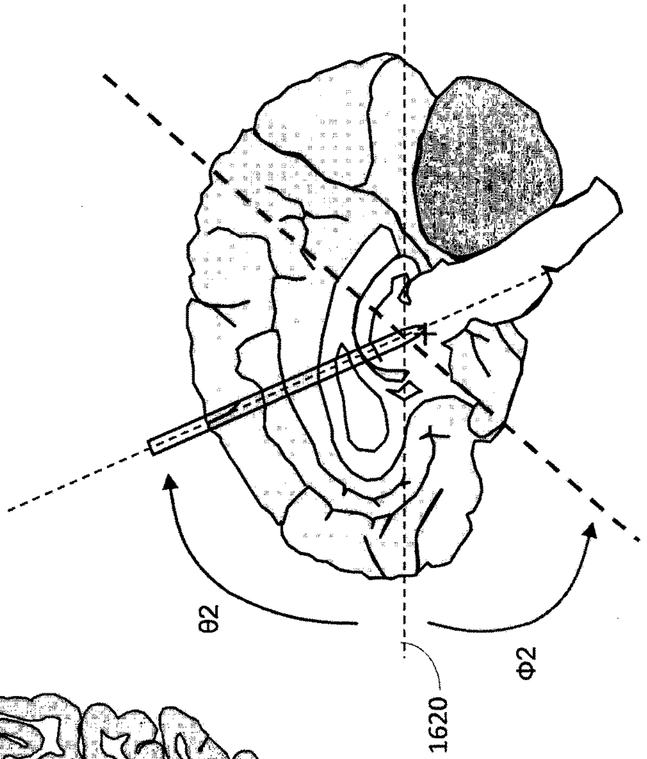

FIGS. 16A, 16B illustrate an example of predetermined orientations of microcoils in the shaft of the device for STN-Gpi projections in a coronal plane view and a mid-sagittal plane view, respectively. An example of a stereotactic target is provided with the reference to the commissure (anterior commissure, AC, and posterior commissure, PC) coordinates of the center of STN: lateral of about 11 . . . 15 mm; anterior-posterior, AP, of about −1 . . . −7 mm; vertical of about −2 . . . −8.5 mm. The center of STN is marked with a "+" sign in FIGS. 16A, 16B. Vertical axis is denoted a 1610, while the AC-PC line is denoted as 1620. In these coordinates, the axis of the shaft of the device is included at an angle $\theta_1$ within the range of 5 to 10 degrees with respect to the axis 1610 and at an angle $\theta_2$ of about 60 degrees with respect to the axis 1620. A chosen microcoil inside the shaft is oriented with its microcoil axis at an angle $\phi_1$ within the range from about 10 to about 20 degrees with respect to the axis 1610 and at an angle $\phi_2$ with the range from about 30 to about 40 degrees with respect to the axis 1620. In a specific implementation, inter-individual variability of the brain-structure may be considered by using MRI scans and/or microelectrode recordings for specific determination (or calibration) of orientations of microcoils in an embodiment of the device. In the case when specific targets are defined (such as, for example, STN-GPi, STN-GPe, and STN-M1 connections, cortical-cortical, cortical-subcortical, and subcortical-subcortical) angles defining the orientations of microcoils can be appropriately adjusted.

An embodiment of the invention may include an electronic circuitry (for example, a computer processor) controlled by instructions stored in a memory. The memory may be random access memory (RAM), read-only memory (ROM), flash memory or any other memory, or combination thereof, suitable for storing control software or other instructions and data. Those skilled in the art should would readily appreciate that instructions or programs defining the operation of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

Disclosed aspects, or portions of these aspects, may be combined in ways not listed above. Accordingly, the invention should not be viewed as being limited to the disclosed embodiment(s).

What is claimed is:

1. A method for stimulation of target neural tissue with a system including a biocompatible shaft having distal and proximal ends and a longitudinal axis and defining a hollow therein, the method comprising:

forming at least one microcoil system that includes a corresponding microcoil characterized by a microcoil axis and that is equipped with a metallic shield element extending along and adjacent to a loop of said microcoil, said forming including juxtaposing said metallic shield element substantially tangentially parallel to a surface defined by said microcoil;

defining an electrical terminal for said at least one microcoil system to receive an electrical waveform from a power source;

defining a first angle based on at least one stereotactic mark associated with a target neural tissue and a second angle describing an orientation of the longitudinal axis with respect to said at least one stereotactic mark to provide, in operation of said at least one microcoil that has been activated by an electromagnetic input applied externally thereto, activation of a neuron having a predetermined orientation in said target neural tissue; and disposing said at least one microcoil system within the hollow that is electrically and fluidly insulated from an ambient medium surrounding the shaft to orient the microcoil axis at the first angle with respect to the longitudinal axis.

2. A method according to claim 1, further comprising disposing first and second microcoils such that their respectively corresponding axes define a region outside of said shaft where a separation between the axes does not exceed a pre-determined value.

3. A method according to claim 1, further comprising activating the at least one microcoil system to form an electrical field that has a non-uniform amplitude in a plane transverse with respect to the longitudinal axis.

4. A method according to claim 1, further comprising defining said at least one stereotactic mark with at least one of a magnetic resonance imaging (MRI) and a magnetic recording of said tissue.

5. A method according to claim 1, further comprising changing a position of said metallic shield element with respect to the corresponding microcoil to modify a spatial distribution of electrical field that has been formed by said corresponding microcoil in response to an electromagnetic input applied thereto.

6. A method according to claim 1, further comprising modulating activation of retinal neurons by forming an electrical field with the use of said at least one microcoil system.

7. A method for stimulation of target neural tissue with a system including a biocompatible shaft having distal and proximal ends and a longitudinal axis and defining a hollow therein, the method comprising:

forming at least one microcoil system that includes a corresponding microcoil characterized by a microcoil axis and that is equipped with a metallic shield element extending along and adjacent to a loop of said microcoil, said forming including juxtaposing said metallic shield element substantially tangentially parallel to a surface defined by said microcoil;

defining an electrical terminal for said at least one microcoil system to receive an electrical waveform from a power source;

disposing said at least one microcoil system within the hollow that is electrically and fluidly insulated from an ambient medium surrounding the shaft to orient the microcoil axis at a first angle with respect to the longitudinal axis;

and changing a position of said metallic shield element with respect to the corresponding microcoil to modify a spatial distribution of electrical field that has been formed by said at least one microcoil system in response to an electromagnetic input applied thereto.

8. A method according to claim 7, further comprising disposing first and second microcoils such that their respectively corresponding axes define a region outside of said shaft where a separation between the axes does not exceed a pre-determined value.

9. A method according to claim 7, further comprising activating the at least one microcoil system to form an electrical field that has a non-uniform amplitude in a plane transverse with respect to the longitudinal axis.

10. A method according to claim 7, further comprising defining the first angle based on at least one stereotactic mark associated with the target neural tissue and a second angle describing an orientation of the longitudinal axis with respect to said at least one stereotactic mark to provide, in operation of said at least one microcoil that has been activated by an electromagnetic input applied externally thereto, activation of a neuron having a predetermined orientation in said tissue.

11. A method according to claim 10, further comprising defining said at least one stereotactic mark with at least one of a magnetic resonance imaging (MRI) and a magnetic recording of said tissue.

12. A method according to claim 7, further comprising modulating activation of retinal neurons by forming an electrical field with the use of said at last one microcoil system.

* * * * *

UNITED STATES PATENT AND TRADEMARK OFFICE
CERTIFICATE OF CORRECTION

PATENT NO. : 9,993,656 B2
APPLICATION NO. : 14/895757
DATED : June 12, 2018
INVENTOR(S) : Shelley Fried et al.

It is certified that error appears in the above-identified patent and that said Letters Patent is hereby corrected as shown below:

In the Specification

Column 6, Line 63, "?" should be --α--.

Column 11, Line 58, "?" should be --$D_p$--.

Column 12, Line 2, "?" should be --σ--.

Signed and Sealed this
Twenty-fourth Day of July, 2018

Andrei Iancu
*Director of the United States Patent and Trademark Office*